(12) United States Patent
Reiner

(10) Patent No.: US 8,957,955 B2
(45) Date of Patent: Feb. 17, 2015

(54) METHOD AND APPARATUS FOR AUTOMATED QUALITY ASSURANCE IN MEDICAL IMAGING

(76) Inventor: Bruce Reiner, Berlin, MD (US)

( * ) Notice: Subject to any disclaimer, the term of this patent is extended or adjusted under 35 U.S.C. 154(b) by 0 days.

(21) Appl. No.: 13/067,749

(22) Filed: Jun. 23, 2011

(65) Prior Publication Data
US 2011/0257919 A1    Oct. 20, 2011

Related U.S. Application Data

(63) Continuation of application No. 11/412,884, filed on Apr. 28, 2006, now Pat. No. 8,018,487.

(60) Provisional application No. 60/675,445, filed on Apr. 28, 2005.

(51) Int. Cl.
| | |
|---|---|
| H04N 7/18 | (2006.01) |
| G01N 37/00 | (2006.01) |
| G06F 19/00 | (2011.01) |
| G06F 17/30 | (2006.01) |
| G06Q 50/24 | (2012.01) |
| A61B 6/00 | (2006.01) |

(52) U.S. Cl.
CPC ............. *G06F 19/321* (2013.01); *A61B 6/502* (2013.01); *G06F 17/3028* (2013.01); *G06F 19/3412* (2013.01); *G06Q 50/24* (2013.01)
USPC .............................................. 348/77; 702/81

(58) Field of Classification Search
USPC ........................................ 348/77, 92; 702/81
See application file for complete search history.

(56) References Cited

U.S. PATENT DOCUMENTS

| | | | |
|---|---|---|---|
| 6,198,800 | B1 | 3/2001 | Garland et al. |
| 6,353,802 | B1 | 3/2002 | Barbur et al. |
| 6,448,544 | B1 | 9/2002 | Stanton et al. |
| 6,611,846 | B1 | 8/2003 | Stoodley |
| 6,704,452 | B1 | 3/2004 | Takeo |
| 6,760,481 | B1 | 7/2004 | Chebil et al. |
| 7,680,308 | B2 | 3/2010 | Dale |
| 7,713,760 | B2 | 5/2010 | Yue et al. |
| 2001/0048027 | A1* | 12/2001 | Walsh ........................... 235/385 |
| 2005/0169425 | A1* | 8/2005 | Takasawa ....................... 378/97 |
| 2009/0028405 | A1* | 1/2009 | Degani et al. .................. 382/131 |

* cited by examiner

*Primary Examiner* — Twyler Haskins
*Assistant Examiner* — Carramah J Quiett
(74) *Attorney, Agent, or Firm* — Jean C. Edwards, Esq.; Edwards Neils PLLC

(57) ABSTRACT

The present invention relates to a computer-implemented quality assurance system, which includes the steps of retrieving quality assurance and supporting information from a database; receiving information on technical variables from monitoring of the patient, and on radiographic equipment in the performance of an imaging study; generating a quality assurance score after said imaging study based on said technical variables and said quality assurance and supporting information; and performing a quality assurance analysis of the imaging study based on the quality assurance score.

30 Claims, 6 Drawing Sheets

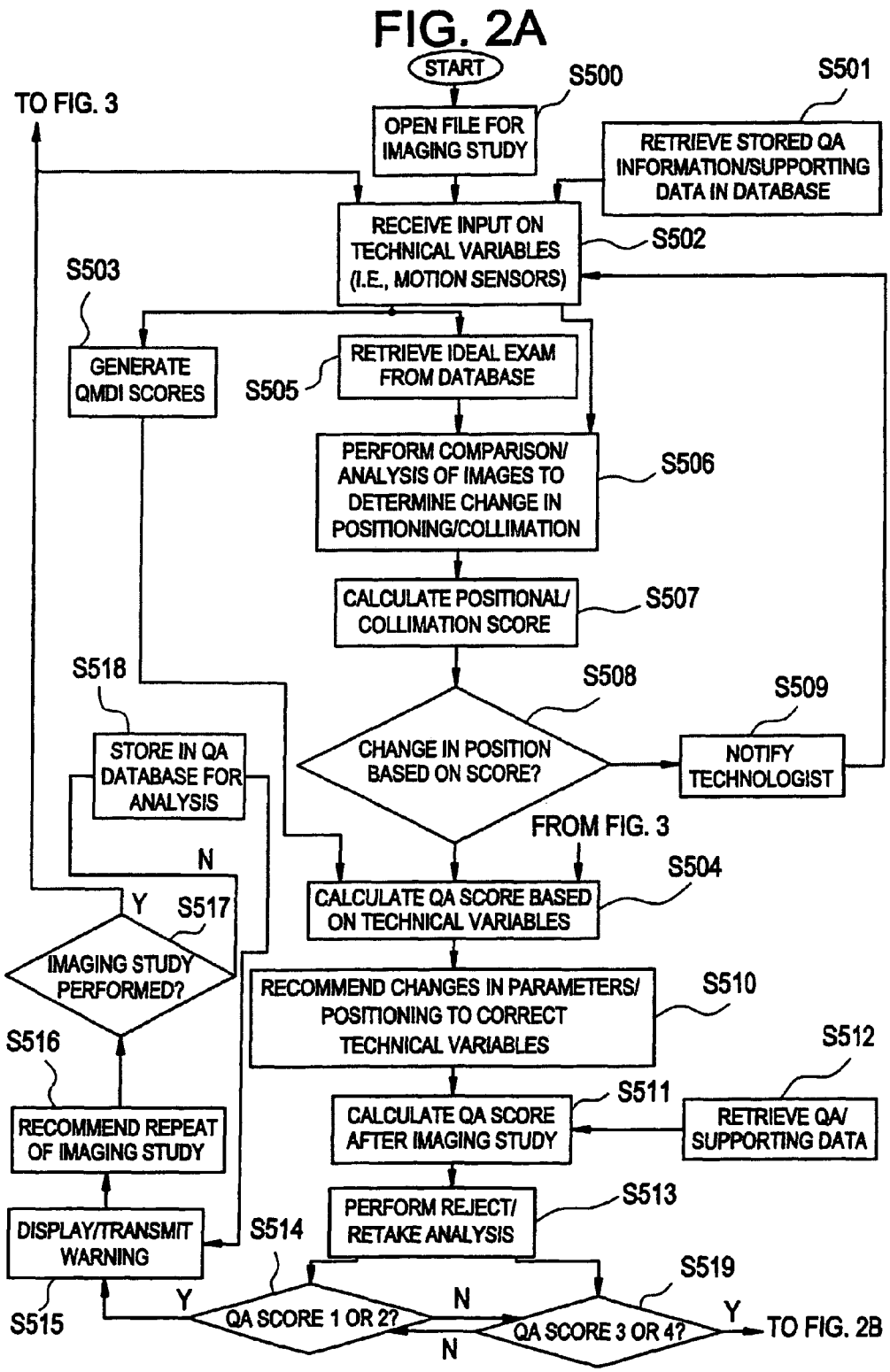

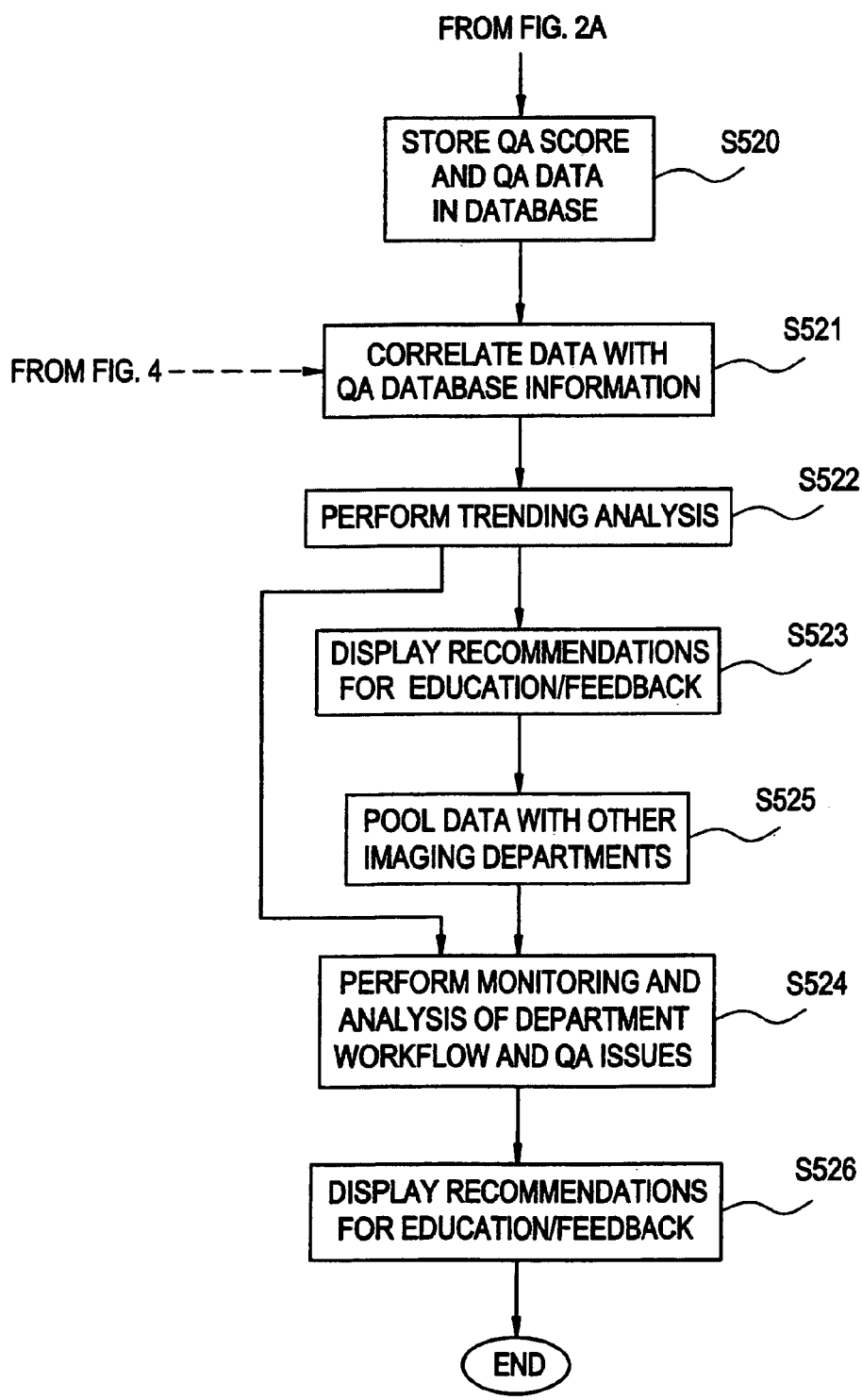

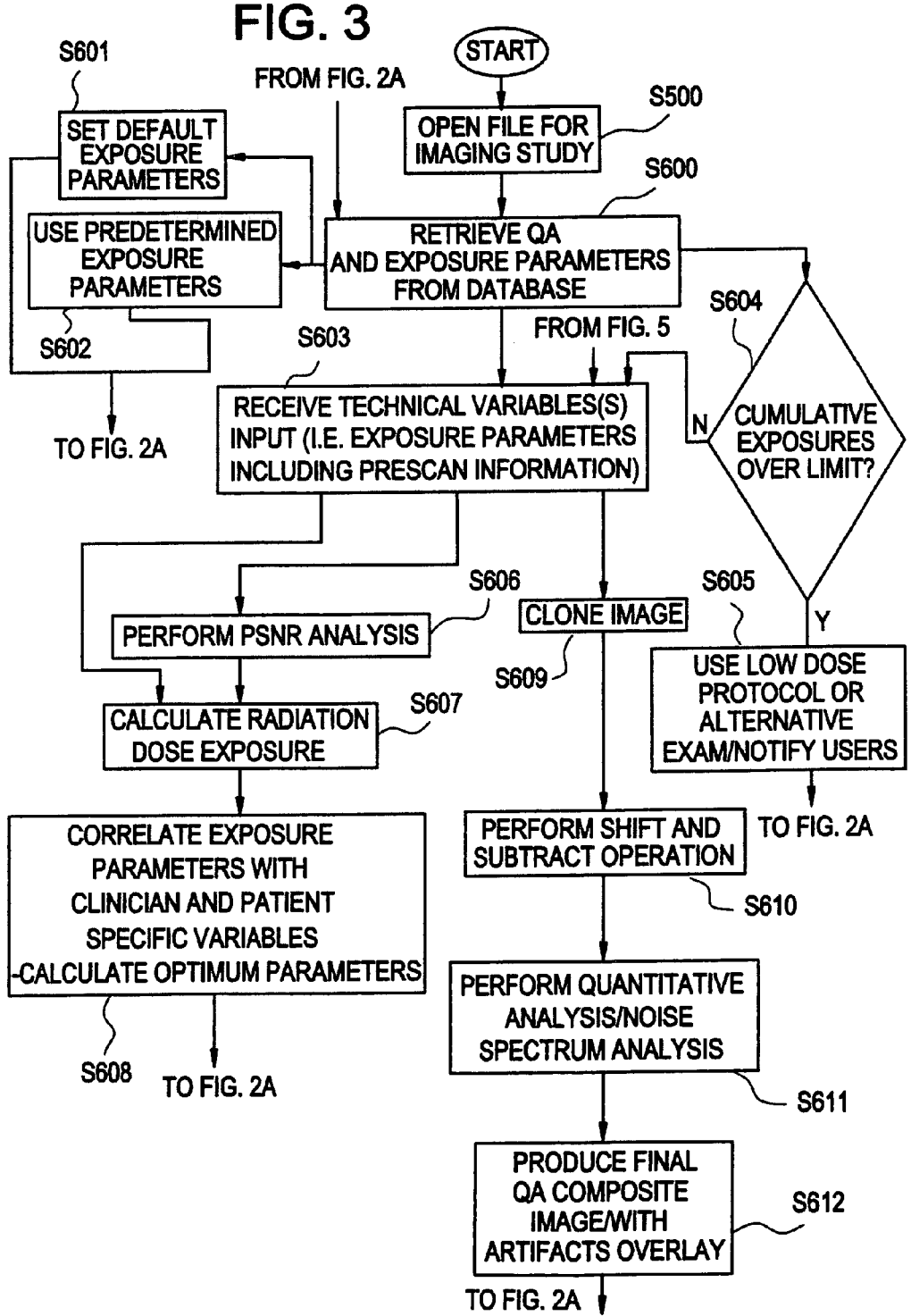

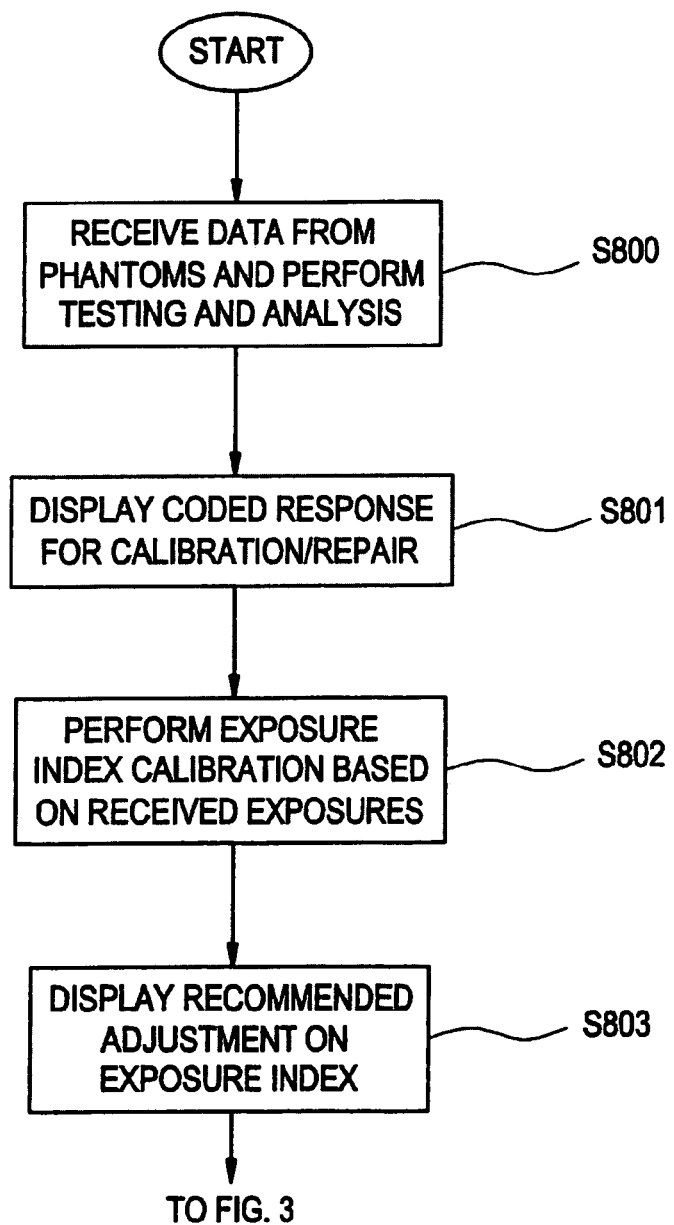

METHOD AND APPARATUS FOR AUTOMATED QUALITY ASSURANCE IN MEDICAL IMAGING

CROSS-REFERENCE TO RELATED APPLICATIONS

This application is a continuation application of U.S. patent application Ser. No. 11/412,884, filed Apr. 28, 2006, which claims priority from U.S. Provisional Patent Application No. 60/675,445, dated Apr. 28, 2005, the contents of all of which are herein incorporated by reference in their entirety.

BACKGROUND OF THE INVENTION

1. Field of the Invention

The present invention relates to a quality assurance (QA) program that can be used in any medical discipline, and in particular in the area of radiology. The present invention is a description of a computer-based software program that converts a manual QA process into an automated one. In the process of doing so, a number of objective data are collected for real-time and future analysis, thereby providing objective feedback to all practitioners for continuing quality improvement. The present invention described, transcends the single process of image acquisition alone, and carries over to the additional processes of image display, interpretation, and reporting. In the end, it is intended to improve patient safety and overall clinical outcomes.

2. Description of the Related Art

The first and foremost priority for any QA program is improved quality of service, and for any medical discipline the ultimate goal is improved patient care. This means that the product or service offers a methodology and the means with which to enhance patient diagnosis and/or treatment, and in doing so objectively improves overall health outcomes.

In the case of medical imaging, the primary focus of attention is the medical imaging exam itself, which provides the means with which to make a diagnosis and initiate or adjust clinical management.

For the last 100 years, the end-product of medical imaging was a hard-copy film, which was displayed on a view box by the radiologist and/or clinician. However, in the past decade, medical imaging has undergone a fundamental transition to digital imaging technologies, which capture, archive, transfer, and display medical imaging studies on computers. This affords the opportunity for medical imaging professionals to leverage the enhanced capabilities of computers to automate what was previously a manual process and utilize computer technologies to manipulate the image in a manner that accentuates certain radiologic features to enhance clinical diagnosis.

While the digital transition has expanded the sophistication of technologies available to medical imaging practitioners, most (if not all) providers still operate in a "film based" workflow model. This means that technologists (who acquire the images), radiologists (who interpret the images), administrators (who are responsible for resource allocation), and vendors (who provide the imaging and information technologies), all maintain a QA focus which is outdated and reflective of the more traditional film-based mode of operation. For all intent and purposes, the end-product (medical image) is still thought of and processed in a manner which emulates film, thereby obviating many of the potential advantages of a film-less operation.

Accordingly, the ability to automate what was previously a manual process and use the inherent intelligence and consistency of computers to objectively perform a variety of functions to enhance data collection, analysis, and feedback, is needed.

SUMMARY OF THE INVENTION

The present invention relates to a computer-based software program that provides an automated QA process for radiology; although one of ordinary skill in the art would recognize that this invention could be applied to other medical disciplines as well as non-medical disciplines.

In the present invention, a number of objective data are collected for real-time and future analysis, thereby providing objective feedback to all users for continuing quality improvement. The present invention as described, transcends the single process of image acquisition alone, and carries over to the additional processes of image display, interpretation, and reporting. In the end, it is intended to improve patient safety and overall clinical outcomes.

In one embodiment, a computer-implemented quality assurance system for radiology, includes the steps of retrieving quality assurance and supporting information from a database; receiving information on technical variables from radiographic equipment in the performance of an imaging study; generating a quality assurance score after the imaging study based on the technical variables and the quality assurance and supporting information; and performing a quality assurance analysis of the imaging study based on the quality assurance score.

In one embodiment, the system further includes correlating information received from the technical variables with the quality assurance and supporting information from the database; and performing a trending analysis. The trending analysis is used to generate recommendations for education and providing feedback to users.

In one embodiment, quantitative motion detection index (QMDI) scores are generated from information on the technical variables; and a quality assurance score is calculated based on motion detection (i.e., motion, position, collimation).

In one embodiment, the system includes retrieving an ideal imaging study from the database; performing a comparison of images from the ideal imaging study and the imaging study, to determine a change in positioning; calculating a positional quality assurance score; and determining a change in position required based on the positional quality assurance score. The quality assurance score is based on a Likert scale of 1-4, wherein 1 is nondiagnostic, 2 is limited, 3 is diagnostic, and 4 is exemplary.

In one embodiment, the system displays a warning to a user when said quality assurance score is 1 or 2, and if so, the imaging study is repeated.

In one embodiment, the system includes calculating a radiation dose exposure based on exposure parameters received from the technical variables. In addition, exposure parameters are correlated with clinician and patient specific variables to determine the quality assurance score.

In one embodiment, the system includes retrieving quality assurance and exposure parameters from the database; and setting default exposure parameters therefrom for the imaging study.

In one embodiment, the system includes retrieving quality assurance and exposure parameters from the database; and using predetermined exposure parameters in the imaging study.

In one embodiment, the system performs a peak signal to noise ratio (PSNR) analysis on the technical variables.

In one embodiment, the system includes cloning an image obtained from the imaging study; performing a shift and subtract operation on the image; performing quantitative analysis on the image; and producing a final quality assurance composite image.

In one embodiment the system includes generating an artifacts overlay for the image.

In one embodiment, the system includes retrieving quality assurance and exposure parameters from the database; and determining whether a cumulative exposure exceeds a predetermined threshold.

In one embodiment, the system includes adjusting a display to user preferences.

In one embodiment, the system includes embedding quality assurance data into user workflow in order to generate quality control profiles on users.

In one embodiment, the system includes creating a best practice template for adherence by users.

In one embodiment, the system includes performing monitoring and analysis of department workflow and user quality assurance issues.

In one embodiment, the system includes receiving data from quality control phantoms and including said data into the technical variables information.

In one embodiment, the system includes performing testing and analysis of the data; and displaying coded responses to a user for calibration and/or repair based on results of the testing and analysis.

In one embodiment, the system includes generating an exposure index adjustment based on the data.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

FIG. 2A is a flow chart of a quality assurance system with respect to technical variables related to motion, according to one embodiment consistent with the present invention.

FIG. 2B is a continuation of the flow chart of FIG. 2A.

FIG. 3 is a flow chart of a quality assurance system with respect to technical variables related to radiation exposure, according to one embodiment consistent with the present invention.

FIG. 5 is a flow chart of a quality assurance system with respect to quality control of the radiographic devices, according to one embodiment consistent with the present invention.

DESCRIPTION OF THE INVENTION

The present invention relates to a computer-based software program that implements a quality assurance (QA) process in a radiological environment.

Figure 1:
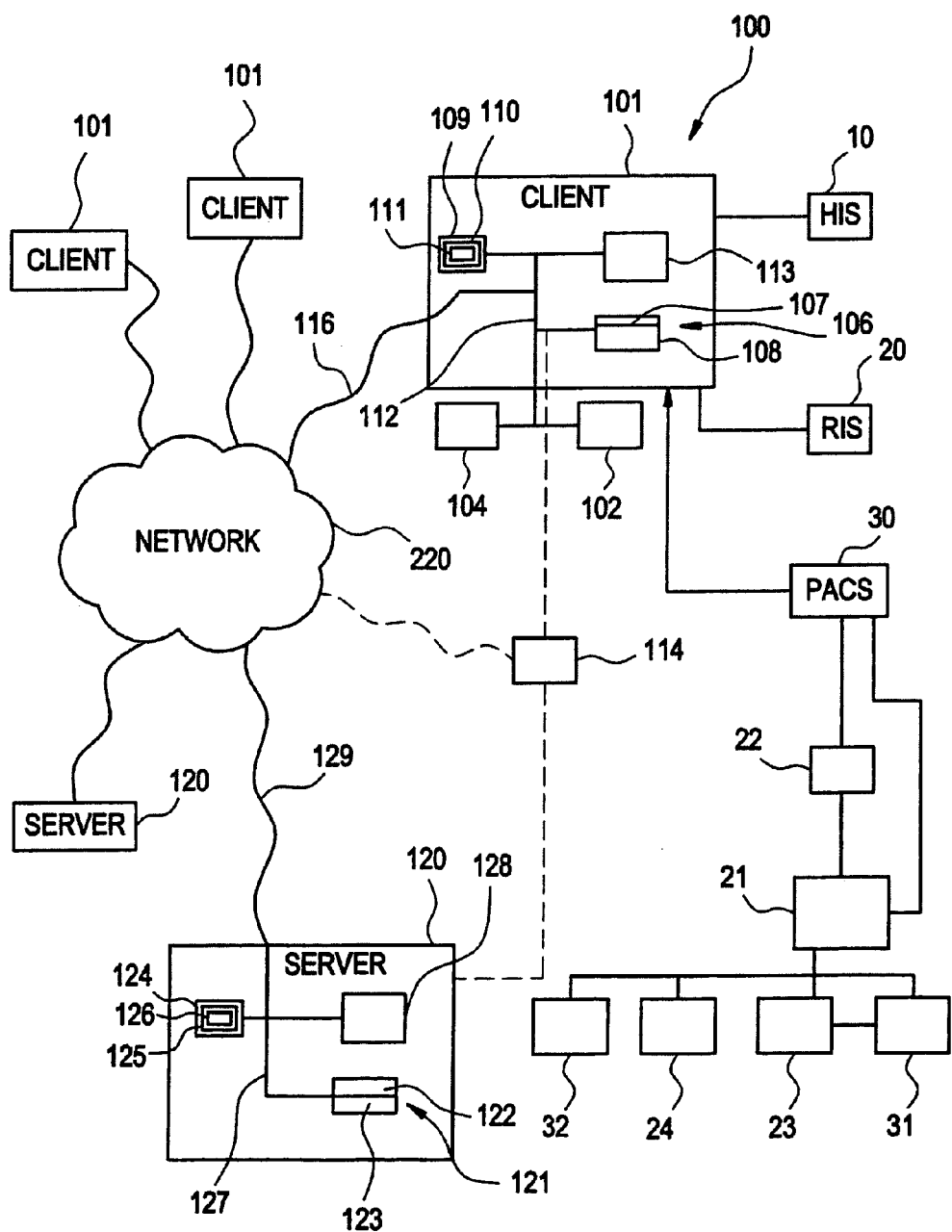
FIG. 1 is a schematic diagram of a quality assurance system for radiology according to one embodiment consistent with the present invention.

In the exemplary embodiment of medical (radiological) applications, the QA system 100 of the present invention (see FIG. 1) is designed to interface with existing information systems such as a Hospital Information System (HIS) 10, a Radiology Information System (RIS) 20, a radiographic device 21 which uses, among others, a computed radiography (CR) cassette or direct radiography (DR) system, a CR/DR plate reader 22, and a Picture Archiving and Communication System (PACS) 30, and conforms with the relevant standards, such as the Digital Imaging and Communications in Medicine (DICOM) standard, DICOM Structured Reporting (SR) standard, or the Radiological Society of North America's Integrating the Healthcare Enterprise (IHE) initiative.

Thus, bi-directional communication between the quality assurance (QA) system 100 of the present invention and the information systems, such as the HIS 10, RIS 20, radiographic device 21, CR/DR plate reader 22, and PACS 30, etc., allows the QA system 100 to retrieve information from these systems and update information therein and provide the desired report generated by the quality assurance system 100.

The QA system 100 of the present invention (see FIG. 1) includes a client computer 101, such as a PC, which may or not be interfaced or integrated with the PACS 30, and includes an imaging display device 102 capable of providing high resolution of digital images in 2-D or 3-D, for example. However, if the image resolution can be sufficiently high, the client may be a mobile terminal, such as a mobile computing device, or a mobile data organizer (PDA), operated by the user accessing the program 110 remotely from the client (see FIG. 2).

Methods and systems consistent with the present invention are carried out by providing an input means 104 (see FIG. 1), or user selection means, including hot clickable icons etc., or selection buttons, in a menu, dialog box, or a roll-down window of an interface provided at the client 101, and the user may input commands through a programmable stylus, keyboard, mouse, speech processing means, laser pointer, touch screen, or other input means 104.

The input or selection means 104 may be constituted by a dedicated piece of hardware or its functions may be executed by code instructions executed on the client processor 106, involving the display unit 102 for displaying the selection window and a stylus or keyboard for entering a selection, for example.

However, input of the symbols or icons, by a user would preferably be accomplished using a multi-functional, programmable stylus 104, which can not only be used to draw symbols onto the image, but can also accomplish other tasks intrinsic to the image display, navigation, interpretation, and reporting processes that are superior to using traditional computer keyboard or mouse methods (both within the PACS and Electronic Medical Report (EMR)).

The client 101 typically includes a processor 106 as a client data processing means, the processor including a central processing unit (CPU) 107 or parallel processor and an input/output (I/O) interface 108, a memory 109 with a program 110 having a data structure 111, all connected by a bus 112. Further, the client 101 would include an input device or means 104, a display 102, and may also include one or more secondary storage devices 113. The bus 112 may be internal to the client 101 and may include an adapter to a keyboard or input device 104 or may include external connections.

The imaging display device 102 for the present invention is a high resolution touch screen computer monitor, which would allow images, such as x-rays, to be readable clearly, easily and accurately. Alternatively, the imaging display device 102 can be other touch sensitive devices including tablet, pocket PC, and plasma screens. The touch screen would be pressure sensitive and responsive to the input of the stylus 104 which would be used to write/draw directly onto the image displaying device 102.

In addition, high resolution goggles may be used to provide end users with the ability to review images without the physical constraints of an external computer.

Note that with respect to the client system 101, the graphics user interface is a client application written to run on existing computer operating systems which may be ported to other personal computer (PC) software, personal digital assistants (PDAs), and cell phones, and any other digital device that has a screen or visual component and appropriate storage capability.

The processor 106 at the client 101 may be internal or external thereto, and executes a program 110 adapted to predetermined operations. The processor 106 has access to the memory 109 in which may be stored at least one sequence of code instructions comprising the program 110 and the data structure 111 for performing predetermined operations. The memory 109 and program 110 may be located within the client 101 or external thereto.

Note that at times the system of the present invention is described as performing a certain function. However, one of ordinary skill in the art would know that the program 110 is what is performing the function rather than the entity of the system itself.

The program 110 which runs the QA method and system of the present invention can include a separate program 110 code for performing a desired operation, or may be a plurality of modules performing sub-operations of an operation, or may be part of a single module of a larger program 110 providing the operation.

The processor 106 may be adapted to access and/or execute a plurality of programs 110 corresponding to a plurality of operations. An operation rendered by the program 110 may be, for example, supporting the user interface, data mining functions, performing e-mail applications, etc.

The data structure 111 may include a plurality of entries, each entry including at least a first storage area that stores the databases or libraries of image files, for example.

The storage device 113 stores at least one data file, such as image files, text files, data files, audio, video files, etc., in providing a particular operation. The data storage device as storage means 113, may for example, be a database, including a distributed database connected via a network, for example. The database can be a computer searchable database and may be a relational database. The storage device may be connected to the server 120 and/or the client 101, either directly or through a communication network, such as a LAN or WAN.

An internal storage device 113, or an external storage device 114 is optional, and data may also be received via a network and directly processed.

In methods and system consistent with the present invention, the client 101 may be connected to other clients 101 or servers 120, including administration, billing or other systems, via a communication link 116 as a client communication means, using a communication end port specified by an address or a port, and the communication link 116 may include a mobile communication link, a switched circuit communication link, or may involve a network of data processing devices such as a LAN, WAN, the Internet, or combinations thereof. In particular, the communication link may be to e-mail systems, fax, telephone, wireless communications systems such as pagers and cell phones, wireless PDA's and other communication systems.

The communication link 116 may be an adapter unit capable to execute various communications protocols in order to establish and maintain communication with the server 120, for example. The communication link 116 may be constituted by a specialized piece of hardware or may be realized by a general CPU executing corresponding program 110 instructions. The communication link 116 may be at least partially included in the processor 106 executing corresponding program 110 instructions.

In one embodiment consistent with the present invention, if a server 120 is used in a non-distributed environment, the server 120 would include a processor 121 having a CPU 122 or parallel processor which is a server data processing means, and an I/O interface 123, but may also be constituted by a distributed CPU 122 including a plurality of individual processors 121 on one or a plurality of machines. The processor 121 of the server 120 may be a general data processing unit, but preferably a data processing unit with large resources (i.e., high processing capabilities and a large memory for storing large amounts of data).

The server 120 also includes a memory 124 with program 125 having a data structure 126 all connected by a bus 127. The bus 127 or similar connection line can also consist of external connections, if the server 120 is constituted by a distributed system. The server processor 121 may have access to a storage device 128 for storing preferably large numbers of program 110s for providing various operations to the users.

The data structure 126 may include a plurality of entries, each entry including at least a first storage area which stores image files, for example, but may also have alternative embodiments including that associated with other stored information as one of ordinary skill in the art would appreciate.

The server 120 may be a single unit or may be a distributed system of a plurality of servers 120 or data processing units, and may be shared by multiple users in direct or indirect connection to each other. The server 120 performs at least one server program for a desired operation, which is required in serving a request from the client 101.

The communication link 129 from the server 120 is preferably adapted to communicate with a plurality of clients.

The present invention is implemented in software which can be provided in a client and server environment, or in a distributed system over a computerized network across a number of client systems. Thus, in the present invention, a particular operation may be performed either at the client or the server, at the edge of a network or at the center, or both. Therefore, at either the client or the server, or both, corresponding programs for a desired operation/service are available.

In a client-server environment, at least one client and at least one server are each connected to a network 220 such as a Local Area Network (LAN), Wide Area Network (WAN), and/or the Internet, over a communication link 116, 129. Further, even though the systems HIS 10 and RIS 20, radiographic device 21, CR/DR reader 22, and PACS 30 (if separate), for example, are shown as directly connected to the client 101, it is known that these systems could be connected to the client over a LAN, WAN, and/or the Internet via communication links. Interaction with users may be through secure and non-secure internet connectivity. Thus, the steps in the methods consistent with the present invention are carried out at the client or at the server, or at both, the server (if used) being accessible by the client over for example, the Internet using a browser application or the like.

The client system 101 may include communications via a wireless service connection. The server system 120 may include communications with network/security features, via a wireless server, which connects to, for example, voice recognition. However, one of ordinary skill in the art would know that other systems may be included.

In another embodiment consistent with the present invention, the client system may be a basic system, and the server may include all of the components necessary to support the software platform of the present invention. Further, the present client-server system may be arranged such that the client system can operate independently of the server system, but that the server system can be optionally connected. In the former situation, additional modules would instead be connected to the client system. In another embodiment consistent with the present invention, the client system and server system can be disposed in one system, rather being separated into two systems.

Although the above physical architecture has been described above as client-side or server-side components, one of ordinary skill in the art would know that the above components of the physical architecture may be in either client or server, or in a distributed environment.

Further, although the above-described features and processing operations may be realized by dedicated hardware, or may be realized as programs including code instructions executed on data processing units, it is further possible that parts of the above sequence of operations are carried out in hardware, whereas other of the above processing operations are carried out using software.

The underlying technology allows for replication to various other sites. Each new site can maintain "state" with its neighbors so that in the event of a catastrophic failure, other server systems can continue to keep the application running, and allow the system to load-balance the application geographically as required.

Further, although aspects of one implementation of the present invention are described as being stored in memory, one of ordinary skill in the art will appreciate that all or part of the methods and systems consistent with the present invention may be stored on or read from other computer-readable media, such as secondary storage devices, like hard disks, floppy disks, CD-ROM, a carrier wave received from a network such as the Internet, or other forms of ROM or RAM either currently known or later developed. Further, although specific components of the system have been described, one skilled in the art will appreciate that the system suitable for use with the methods and systems consistent with the present invention, may contain additional or different components.

Accordingly, in one embodiment consistent with the present invention, the QA system 100 and method as used in an exemplary radiology method and system, includes a client computer 101 with image displaying device 102, and an input device 104. An image study is taken of the patent by a technologist based on a physician's instructions, using the radiographic device 21, and the cassette is read at plate reader 22, and the images forwarded to the PACS 30, and then to the computer imaging display device 102 for display and storage. The images can be stored, analyzed and utilized in the QA method and system of the present invention, or discarded.

In particular, the following describes in more detail, the QA system and method of the present invention.

A. Technologist QA Data

Specifically, during the process of taking the medical image, the technologist will position the patient at an examination table for the radiographic device 21 to capture the radiographic images. The radiographic device 21 will obtain certain QA data during the imaging study which is forwarded to the client 101 and recorded by the computer program 110 when the medical image is taken.

In one embodiment consistent with the present invention, QA for the radiographic process is directed to correcting for technical deficiencies occurring in the image acquisition portion of the imaging study. These technical deficiencies can be the result of patient non-compliance (e.g., motion), technologist oversight (e.g., positioning), or technology malfunction (e.g., artifacts).

In the end, the automated QA program 110 of the present invention is responsible for identification and analysis of these technical deficiencies and provide immediate feedback to the various users (e.g., technologists, administrators, radiologists).

The QA data which is obtained by the program 110 during the image acquisition, includes the following technical variables: 1) motion, 2) positioning, 3) exposure, 4) artifacts, 5) collimation, and 6) supporting data—which are discussed in more detail below.

After the program 110 obtains data on these technical variables, the computer program 110 automatically calculates a score for each of the above technical variables along with the supporting data which includes patient and exam-specific identifying data, for each imaging exam taken by the technologist.

The client 101 is programmed to score the technical QA variables listed above, on a computer-generated Likert scale of 1-4, using the following definitions for the scale:

A score of 1 is "non-diagnostic". This means little or no clinically useful (diagnostic) information is contained within the image obtained. Since the available information obtained during the examination of the patient does not answer the primary clinical question (i.e., indication for the study), then by definition this requires that the imaging exam be repeated for appropriate diagnosis.

A score of 2 is "limited". This means that the information contained within the image obtained is less than expected for a typical examination of this type; however, it is sufficient to answer the primary clinical question. The requirement that this exam be repeated is not absolute, but is preferred, in order to garner maximal diagnostic value.

A score of 3 is "diagnostic". This means that the information contained within the image is representative of the broad spectrum of comparable images, allowing for the patient's clinical status and compliance. Both the primary clinical question posed, as well as ancillary information, can be garnered from the image for appropriate diagnosis.

4) A score of 4 is "exemplary". This means that the information contained within the image and overall image quality serves as an example that should be emulated as the "ideal" for that specific imaging study and patient population. As stated above, the QA score is affected by the technical variables noted above of: 1) motion, 2) positioning, 3) exposure, 4) artifacts, 5) collimation, and 6) supporting data.

1) Motion

Motion is one of (if not the most) important QA limiting factor in medical imaging, regardless of the imaging modality. Almost all imaging modalities (with the exception of ultrasound) are acquired in a static mode, thereby creating the opportunity for motion to adversely affect spatial resolution and in turn compromising diagnostic accuracy. Since the offending culprit is the patient, in one embodiment, motion sensors 23 are positioned directly onto the patient in order to maintain the highest accuracy (see below for further discussion).

For the portable intensive care unit (ICU) exam, minimal motion would be customary, in light of the inability for the comatose patient to voluntarily hold their breath and remain completely still while the examination is being conducted. The more compliant ambulatory patient, on the other hand, would be able to stand still, follow verbal commands, and refrain from respiratory and voluntary motion during the course of the exposure.

As a result, what is considered to be diagnostic for these exams (in terms of "motion"), is far different. The ICU portable chest image may have minor respiratory motion that produces minimal blurring of the lung parenchyma, but provides the ability to accurately detect the presence or absence of pneumonia, which is the stated clinical indication.

As a result, this exam would receive a QA motion score of "3" (diagnostic), for example, from the computer program 110, for this technical variable alone (see FIG. 2A, steps S511, S513, and S519). If on the other hand, the degree of respiratory motion caused a slightly greater degree of blurring that resulted in partial obscuration of the diaphragm and tip of an indwelling central venous catheter, the QA motion score would now be calculated by the computer program 110, as a "2" (limited). With a score of "2", the lung fields are shown with enough clarity such that they can be assessed for the presence or absence of pneumonia, but other important anatomic regions and critical structures are partially obscured in the image.

The more extreme QA motion scores of "1" (non-diagnostic) and "4" (exemplary) would correspond to a portable ICU chest radiographic image that is completely obscured by motion, and the opposite image that is completely devoid of motion.

If the ICU portable chest radiograph was compared with a standing ambulatory chest radiograph, the evaluation and scoring of the technical QA variables by the computer program 110, would vary significantly, based on the different expectations in image quality for these two examinations which are obtained for the same anatomic regions and clinical indications.

In another example, the standing chest radiograph performed in the post-operative ambulatory patient is also performed in the evaluation of pneumonia. In this clinical setting and patient population, the expectations for image quality are different, based on differences in patient compliance, clinical status, and technique. The standing chest radiograph is performed on a wall-mounted Bucky unit, that provides for overall improvement in image quality. At the same time, the patient is capable of following the verbal commands of the technologist and can suspend respiration in full inspiration, thereby maximizing lung volume and visualization of potential lung parenchymal pathology (such as pneumonia). The ICU patient, on the other hand, could not control breathing and was in a supine, dependent position, resulting in poorly inflated lung fields, prone to motion.

For this standing chest radiographic image, the QA expectations are obviously different. Minimal motion that blurs the lung parenchyma would in this instance receive a QA motion score of "2" (limited), due to different expectations for the different patients and techniques employed.

Accomplishing the detection of motion in the present invention, can be performed in a number of ways.

In one embodiment consistent with the present invention, determining motion detection (and thus, determining the QA motion score) entails the placement, by the technologist, of miniature transparent motion phantoms 23 directly onto the patient skin surface prior to the imaging study. These motion phantoms 23 can take a number of different forms, with some possible candidates listed below:

¥ ▓ ● ≡

These motion phantoms 23 would be positioned at multiple points on the patient's skin surface within the field of view. The computer program 110 would generate a quantitative motion detection index (QMDI) score (see FIG. 2A, step S503) based on movement, blurring, or contour irregularity of each phantom image, which is superimposed directly over the medical image. The transparency of the phantom image would avoid having any important information contained within the medical image from being obscured during the image review and interpretation process.

These QMDI scores would then be correlated by the computer program 110 with a number of variables—including the anatomic region being imaged, the modality, patient physical characteristics, and clinical indication, to determine a QA motion score (on the Likert scale above), and therefore, to determine whether the quantified amount of motion is deemed acceptable (see FIG. 2A, step S504).

For example, obtaining QMDI scores in clinical practice can be illustrated with mammography. Depending upon the patient's body habitus (i.e., breast size) and pathology being analyzed, the degree of "acceptable motion" may vary. If for example, the pathology being analyzed is a mass or density (which is more dependent on contrast and not spatial resolution for detection), modest degrees of motion would be deemed acceptable for diagnosis.

If instead, the pathology being evaluated is microcalcifications (which are highly dependent upon spatial resolution), then relatively small measures of motion will not be acceptable. In that case, the QMDI score may be calculated by the computer program 110 based on the motion of the phantom images 23 in view of the other variables (anatomic region, modality, etc.) (see steps S503, S504). For example, the QMDI scores are recorded by the program 110 along with the exposure parameters, breast compression (measured in Newtons), number and type of views, field of view, and compression device utilized (along with post-image processing applied). The QMDI score obtained is then automatically correlated by the program 110, for example, to a QA motion score of "1", or "non-diagnostic" which is displayed for the technologist (see steps S514, S515). The technologist will then be directed by this score, to repeat taking the radiographic image (see step S516), with computer program-recommended technical modifications (such as increasing the degree of breast compression, and using a smaller compression paddle and field of view), which are recommended based on the QMDI score and QA data detected. Further, existing decision support computer-aided detection software, which is currently in everyday use, can be mapped to the motion computation device (i.e., motion phantoms 23) to correlate the QMDI score with the pathology in question.

In another embodiment consistent with the present invention, the detection of motion during medical imaging would include using nanotechnology in the form of microscopic motion detection sensors 24 that can provide real-time (i.e., instantaneous) motion feedback directly to the radiographic acquisition device 21 (see steps S502, S504, S510). If this nanotechnology motion sensor 24 is correlated with existing gating technology (e.g., cardiac gating), then the acquisition device 21 can be temporally directed by the computer program 110 as to the exact moment of minimal physiologic and patient-induced motion, to initiate image capture by the radiographic device 21. This technology is best suited for complex cross-sectional imaging modalities (e.g., CT and MRI) which are evaluating anatomic regions and types of pathology exquisitely sensitive to small amounts of motion, which preclude accurate diagnosis.

Cardiac CT and MR angiography would be two examples of non-invasive imaging modalities which are currently limited (in diagnostic efficacy) by extremely small amount of motion. In this example, the nanotechnology motion sensors 23 would be directly placed over the anatomic regions of interest (e.g., right and left ventricles) and directly calibrated with the CT detection sensors and EKG gating device to coordinate respiratory, cardiac, and patient-induced motion. When the desired component of the cardiac cycle begins and external motion detection is minimal, as detected by the detection sensors 24 (see step S504), the CT acquisition would be activated by the computer program 110. The QMDI calculated by the computer program 110 (see step S503), and displayed and stored in the database 113 (see step S511, S518, S520), can in turn be incorporated into the interpretation process and into the report (by the cardiologist or radiologist) to ensure quantitative measures of coronary arterial stenosis are accurate and not adversely affected by QA limitations (see step S521).

In another embodiment consistent with the present invention, in addition to motion sensors 23 (in macroscopic and microscopic forms), another type of motion detection uses reflective devices 31. The reflective device 31 (e.g., transparent mirror) is placed directly onto the patient's anatomic region of interest and light from a laser on the imaging modality is reflected onto the mirror 31. The reflected light is in turn processed by a motion sensor 24 (using signal processing analysis), and a microprocessor 106 with computer program 110, to determine the magnitude and directionality of motion. This calculated QMDI in turn, is entered into a comprehensive motion database 113 of the client 101, that can be categorized by specific patient, modality, anatomic region, and clinical indication to correlate QMDIs with clinician image QA scores (see step S520). These scores (on the Likert scale) can then be used to determine clinically acceptable levels of motion relative to each exam type and clinical indication.

2) Positioning

With respect to the next technical variable—positioning—the evaluation of image quality is also dependent upon the positioning of the exam (i.e., portable, upright, standing) and patient factors (i.e., body habitus, clinical status, compliance).

Expectations for image quality would obviously vary for a portable examination performed on a comatose patient in the intensive care unit (ICU), as opposed to a standing chest radiograph for an ambulatory (and relatively healthy) outpatient. Technical deficiencies related to position are most frequently encountered with general radiographic and mammographic imaging studies.

In order to ensure proper positioning in an automated manner, the computer program 110 must correlate the current imaging exam with a comparable "ideal" exam (see FIG. 2A, step S505), which is contained within a digital database 113 of optimized images. Each individual examination and the multiple images contained with the comprehensive image data set would be cross-referenced by the computer program 110 with the "idealized" template images within the database 113. Using computerized pattern recognition and segmentation, the computer program 110 can then compare the two imaging datasets to determine if positioning of the individual images has been altered (see step S506), and to notify the technologist with a display or alarm (i.e., sound or visual display) (see step S509).

One way to accomplish this would be to utilize the transparent motion sensors 23 previously described as localizers for anatomic positioning. These sensors 23 could be positioned at predetermined locations within the anatomic region of interest. If for example, these motion sensors/anatomic localizers 23 are positioned at the four corners and center of the field of view, the computer program 110 can simultaneously compute the motion index and spatial orientation of the desired anatomic region. If a technologist is acquiring an AP chest radiograph, he/she would position the sensors 23 over each shoulder and the inferolateral aspect of the $12^{th}$ anterior ribs. This would in effect define the perimeter of the image, with a fifth sensor 23 positioned over the xiphoid process denoting the center. Since all patients would in effect have the same anatomic markers, reproducibility of this system would be consistent from patient to patient and technologist to technologist.

If the same task was performed on a more complicated five-view cervical spine radiographic exam, the same system of anatomic markers (two sensors 23 over each mandibular angle, two sensors 23 over the mid aspect of each clavicle, and a single centrally positioned sensor 23 over the thyroid cartilage (i.e. Adam's apple)) would be utilized. These sensors 23 would remain fixed in location for each of the five views including the AP (i.e., frontal), lateral, oblique, and open mouth views. Since the standardized reference (ideal) images would have the same anatomic reference markers, the computer program 110 would compare both sets of images (see step S506) to ensure the appropriate region is included in its entirety, as well as the orientation of the anatomic structures contained within the image are similar. The greatest positional challenge for this type of exam would be the oblique views, which should have the intervertebral foramina (where the nerve roots exit the spine) viewed en face (which creates the appearance of looking directly into a longitudinal series of round holes). Using computerized pattern recognition, the computer program 110 can analyze and record the degree of concordance and create a quantifiable positional score, highlighting any areas of significant discordance (see step S507).

These individual and collective computerized "positional scores" would then be displayed as a QA score (see step S511), and the QA score could then be recorded into the technical component of the QA database, and be supplemented by the radiologists' and clinicians' image quality scores (as they relate to position) (see the discussion below). If an individual technologist or group of technologists has certain types of exams shown to have positional deficiencies, then educational and training programs (e.g., in-services) could be targeted to these specific problem areas (see FIG. 2B, step S526). By providing objective (and automated) instantaneous feedback to the technologist at the time of image acquisition, it is anticipated that patient delays, call backs, and exam retakes would be reduced, along with overall improvement in image quality.

3) Exposure

The next technical QA variable to analyze is "exposure", which ultimately affects both contrast and spatial resolution of the chest radiographic image. For this QA variable, anatomic region and clinical indication take on even greater importance. Accurate detection of a small lung nodule would be more dependent upon subtle differences in contrast resolution, while interstitial lung disease or a non-displace rib fracture would be more dependent upon subtle differences in spatial resolution. As a result, the technical QA exposure score must take into account the clinical indication and anatomic region being evaluated.

Exposure parameters currently used in medical imaging are to a large extent idiosyncratic and highly variable from one technologist and one institution to another. In order to maximize signal to noise ratio (i.e., minimize image noise), and optimize image contrast, many technologists (and radiologists) elect to use higher mAs and kVp settings, which result in higher radiation doses.

For general radiographic examinations, the current standard for determining exposure time utilizes a photo-timer, which automatically terminates the exposure once a certain radiation dose is registered by a sensor. The problem with this technology is that it does not adequately take into account unique differences in patient body habitus, previous surgery, or underlying pathology. The exposure is controlled at one of a few limited points by the use of these strategically based detectors which do not do an adequate job of anticipating the optimal exposure factor for the entire patient.

If for example, a patient has severe emphysema (causing the lungs to become over-inflated), the photo-timer will prolong the appear "too black". The opposite occurs when a patient has a large pleural effusion (causing one side of the thorax to be lighter than the other, since fluid is denser than air). In this opposite scenario, the photo-timer will prematurely terminate the exposure, thereby causing the radiographic exposure to be under-penetrated or "too light". Similar exposure deficiencies occur when patients have excessive size differences or surgical hardware present.

In one embodiment consistent with the present invention, the exposure parameters collected during the image study can be stored in the computer database 113, i.e., within the acquisition device 21 and DICOM header. The client 101 can be programmed to automatically transfer the exposure parameters to the individual exam and QA database 113 (see FIG. 3, step S600), and the computer program 110 can use these parameters to automatically calculate radiation dose exposure (see step S607) based on a pre-defined formula for each exam type and anatomic region.

The purposes of recording this data are to: 1) calculate radiation exposure doses for each exam, where a patient-specific dose exposure can be cumulatively tallied and monitored by the computer program 110 (which is of increasing importance as more medical imaging is used for screening purposes), and 2) correlate the exposure parameters with the overall QA database 113 to optimize image quality and patient safety in the following manner.

In one embodiment, the computer program 110 correlates the exposure parameters with similar exam types (from other patients) and cross-references the exposure parameters with corresponding image quality scores (as reported by the interpreting radiologists) (see step S608). Thus, computer-generated recommendations for "optimum" exposure parameters are produced and displayed (see step S608) for the user by the program 110, for eventual QA scoring (see step S511).

In another embodiment, the exposure parameters can be correlated by the computer program 110 (see step S608), with a number of clinical and patient specific variables to predict how variation in the exposure parameters can be further optimized. Patient and specific factors could include body habitus, interval weight gain or loss, mobility, and compliance. Clinical factors could include underlying medical conditions and indications for performing the requested exam.

In one example, a patient is referred for a chest radiograph to evaluate chronic cough. By the user accessing additional data from the electronic medical record (EMR), the program 110 displays the information that the patient is morbidly obese, but has experienced significant (and unexplained) weight loss of 100 pounds over the past 6 months. The patient's past medical history is significant for a long smoking history resulting in chronic obstructive pulmonary disease (COPD), which caused the lungs to be hyper-inflated. The patient's obesity, recent weight loss, and underlying COPD all have important relevance to the selection of optimized exposure parameters. By the user querying the QA database 113 for relevant data, the computer program 110 can automatically provide the technologist with recommended exposure parameters (see step S608). The additional history of longstanding smoking and chronic cough is a predictor of lung cancer, which also provides valuable information on specific image processing parameters to be used for improved diagnosis of lung cancer.

The patient's historical medical imaging data can be accessed by the user from data stored in the radiology information system (RIS) 20 and picture archival and communication system (PACS) 30. This can provide previous exposure parameters for the same patient and same (or similar) imaging exams, along with the corresponding image quality scores (see step S600). If for example, a previous mammogram had an overall image quality score of 95 (out of a possible 100), the computer program 110 could present the technologist with the specific exposure parameters employed at the time of the prior exam and automatically set this as the default exposure parameters for the current study (see step S601).

When a patient's cumulative radiation dose exposure has exceeded a predefined limit stored in the QA database of the computer, the computer program 110 can issue an alert (by display, e-mail message, and/or audible alarm) to the referring clinician, radiologist, technologist, medical physicist and administrator (see step S604). (In addition, the computer program 110 can automatically prepare an e-mail message or letter that can be sent directly to the patient with a detailed explanation of risks and alternatives (see step S605).) This information can in turn be used to supplement efforts for reducing radiation exposure by programming the computer to use specialized low dose protocols (e.g., CT), advising the replacement of imaging exams with ionizing radiation for those without (e.g., MRI in lieu of CT), and analysis of future imaging exam requests (see step S605). This is of particular importance to oncology patients, who undergo frequent and repetitive imaging studies during the course and immediately following their cancer diagnosis and treatment.

In addition to recording exposure parameters for each imaging exam, specific protocol parameters are recorded in the database by the computer program 110, for the program 110 to cross-reference these parameters with clinical data pertinent to the exam indication, laboratory data, and diagnosis. These protocol parameters are especially valuable for the computer program 110 to cross-sectional imaging modalities such as computed tomography (CT) and magnetic resonance imaging (MRI).

For example, in the case of a patient who is being followed for a small 1 cm right lung cancer, which has been treated with chemotherapy and radiation therapy—on prior exams, the cancer was best visualized using 0.5 mm collimation using a high-resolution protocol. Knowing this specific protocol provides the optimum comparison can not only improve diagnostic accuracy, but also reduce radiation exposure by minimizing the use of additional and unnecessary imaging sequences. In addition, the specific post-acquisition processing parameters previously employed can be automatically applied by the computer program 110 to ensure direct comparison with the historical comparison study (see step S522).

In one embodiment, the present invention would optimize exposure parameters and utilize a "pre-scan", which consists of an ultra low dose exposure (approximately $\frac{1}{20}^{th}$ the customary dose of conventional exposure parameters) (see step S603). This "pre-scan" would create a pixel density map of the anatomic region imaged, which can be displayed and stored by the computer program 110. The computer program 110 would then perform a histogram analysis of pixel density of the pixel density map to compute the optimum exposure parameters, taking into account both image quality and radiation dose. Because the pixel density map would be specific to each individual patient, modality, anatomic region, and underlying pathology, the calculated exposure parameters would be individually optimized, can be displayed by the computer program 110 (see step S608), and stored in the QA database for future reference (see step S520). This pixel density map could then be retrieved by the technologist in the future when he/she is repeating the same type of exam, thereby improving image quality, consistency, and workflow (see step S600).

When calculating a computer-generated correction for the mAs and kVp, additional technologies could be employed "on the fly" to balance the requirement for optimized contrast resolution and dose reduction. In another embodiment consistent with the present invention, the computer program 110 could perform an existing peak analysis to noise ratio (PSNR) analysis (see step S606), which evaluates the variability in pixel data to quantitatively measure the amount of noise contained within the medical image. The computer program 110 can then perform an analysis to minimize noise and maximize signal, in order to optimize overall image quality. Using this PSNR technology, the computer program 110 can in turn, calculate the inflection point at which dose reduction can be achieved without causing clinically significant degradation in image quality (see step S607).

Additional factors that can go into the analysis performed by the computer program 110, would include the patient's radiation history (i.e., cumulative radiation dose), the clinical indication for the exam, and pre-existing medical history. For example, a patient undergoing a chest CT exam to follow up treatment of a pre-existing lung cancer could have a study specifically targeting the documented site of cancer. The computer can be programmed to correlate this study with previous CT exams and the pertinent medical history stored in the database. The "pre-scan" can be performed directly over the area of known tumor. The pixel density map obtained over this pre-defined area of interest (see step S603) can then be analyzed by the computer program 110 in conjunction with the PSNR analysis (see step S606) to produce a computer-generated correction for mAs and kVp that provides the required diagnostic information at the lowest possible radiation dose to the patient (see step S607). This strategy is particularly beneficial in the pediatric patient populations where cumulative radiation dose takes on heightened importance. Since traditional image processing is currently performed "after the fact" with the purpose of accentuating pathology and reducing noise within the medical image, the strategy of the present invention to optimize exposure during the image acquisition process is unique in that it is prospective in nature. The data collected is automatically entered into a QA database 113 (see step S520) that can be searched, and which can be used for technologist education and training, development of decision support software, and patient outcomes analysis (see step S523).

In another embodiment consistent with the present invention, the computer can be programmed to apply a predetermined exposure to each image taken (see step S602). Since digital radiography provides medical imaging with the ability to utilize computer-based tools and image processing to enhance diagnosis, these decision support tools can be customized to the end-users preferences, specific clinical indication, and anatomy being evaluated. These "user specific", clinical, and anatomic profiles can in turn be archived in the computer database and automatically applied (see steps S501, S502).

4) Artifacts

The next QA variable is artifacts. Artifacts represent signals within the detected and displayed image that are unwanted and degrade the ability to make an accurate diagnosis. These signals arise from various sources, including:

the x-ray detector (e.g., flat panel defects such as detector element dropouts and column and row malfunction, scratches or debris on CR imaging plates, poor compensation for signal shading and flat-field corrections);

b) components within the x-ray system projecting non-uniform or periodic signals onto the detector (e.g., antiscatter grid—either non-moving or inappropriate motion during the exposure, debris such as contrast agent on the detector cover, high density materials on the x-ray tube filter(s), inappropriate positioning of compensation filters to reduce dynamic range);

c) the patient (e.g., involuntary or voluntary motion during the exposure, external high-density objects such as overlying EKG leads, earrings, necklaces and makeup).

Artifacts are a major impediment to correct diagnosis. QA scoring of artifacts is to some extent dependent upon the exam type, patient profile, the anatomy being evaluated, and clinical indication. For example, for the portable ICU chest radiograph, a number of artifacts can be identified, which are to some extent expected and unavoidable. These critically ill patients are often on multiple monitoring devices (e.g., EKG leads) that cannot be removed for the imaging exam. While these partially obscure the underlying anatomy within the chest, it is a limitation that must be accommodated for to take the radiographic image.

If on the other hand, EKG leads or snaps were present on the stable, ambulatory patient obtaining a standing chest radiograph, these would not be considered to be essential and could be temporarily removed to enhance image quality.

The QA technical artifact scores for these two different situations would be calculated differently by the computer program 110, based on unique differences in the patient profiles and clinical status.

Another extraneous artifact that can be avoided would be that of a skin fold which often produces an artifactual line over the lateral chest. If for example, the portable chest radiograph is being performed to evaluate pneumonia, this artifactual line would not adversely affect the ability to render diagnostic interpretation and would therefore receive a technical QA score of "2" (limited). If however, the clinical indication is to evaluate recent placement of a central venous catheter, then this QA score would now change to a "1" (non-diagnostic) because the skin fold can mimic the radiographic appearance of a pneumothorax, which is a clinically significant complication of central line placement. While the artifacts would have the same appearance, the clinical indication would necessitate a repeat exam in one case but not the other.

Detection and localization of image artifacts are crucial, and quality control procedures needed to identify, and determine the cause, and correct the artifact, is desired in order to achieve optical image quality.

For artifacts due to x-ray detectors, one embodiment consistent with the present invention to automatically identify, determine the direction, and localize the extent to the artifacts present is, to perform a uniform x-ray exposure, fully irradiating the detector to 50% of its dynamic range, using a long x-ray tube to detector distance, a typical exposure time (e.g., 50 ms), and appropriate kV and mA settings with no grid.

The acquired image is then cloned by the computer program 110 (see FIG. 3, step S609), and the two identical images are shifted by a number of pixels with respect to each other in a specific direction by the program 110 (e.g., four pixels in the row direction for the cloned image) (see step S610). The computer program 110 would then subtract the two images (maintaining the negative and positive differences) of the operation and ignoring the edge effects), and add an offset signal, yielding a "shift and subtract" image (e.g., SS 4x 0y) for a given shift direction and number of pixels (see step S610).

The "shift and subtract" operation by the computer program 110 yields a difference image which is displayed by the program 110 on the monitor (see step S610), and delineates artifacts by creating negative and positive artifact signals with amplitudes greater than the subtracted image noise variation, and at the same time reduces low frequency variations that are not likely to be important. Linear artifacts perpendicular to the shift direction will generate extensive artifact signals, while linear artifacts parallel to the shift direction will generate only small difference signals at the periphery of the artifact. Contrast enhancement of the difference image by the computer program 110, provides a quick qualitative check for the presence of artifacts for a single shift and subtract operation. Note that some structures in the direction of shift are self-cancelling; also, subtle artifacts difficult to appreciate in the original image are now easier to detect.

Quantitative analysis is performed by the computer program 110 (see step S611) evaluating the total image with adjacent small region of interest (ROI) boxes (e.g., 64×64 pixel or other area), calculating the Standard Deviation (SD), and encoding the values with a grayscale or color output scale.

Multiple shift and subtract operations in horizontal, vertical, and combined directions, by the computer program 110, fully map the extent and locations of the artifacts (see step S611). Summation of the individual difference images using a common coordinate position by the computer program 110, produces a composite summation image with obvious and subtle artifacts clearly delineated (see step S612). Identification of regions with significant artifacts can be recognized by the computer program 110 mapping the SD values from the ROI areas in a grayscale or color scale as an overlay on the composite image. The procedure is implemented by the computer program 110 using an automated algorithm to produce the final QC composite image and an overlay map of areas with artifact generating signals (see step S612).

Artifacts generated from other components, requires a uniform attenuator (e.g., 15 cm uniform plastic, of a size to cover the majority of the detector area), antiscatter grid assembly, and typical patient acquisition geometry. A similar procedure as described above for image processing and analysis (shift and subtract) is used for automated analysis of artifacts using a computer program 110 (with knowledge of any intrinsic detector artifacts per the initial evaluation). Additionally, noise power spectrum analysis (see step S611) is applied by the computer program 110 to the image, to determine specific spatial frequencies with increased noise contributions, such as that produced by a non-reciprocating grid and its associated frequencies and/or aliased signals.

5) Collimation

With respect to the next technical variable of collimation, QA scoring is related to that of positioning. Improper collimation can result in certain critical areas of anatomy being excluded from the imaging study (excessive collimation) or result in too much anatomy being exposed and displayed on the image (insufficient collimation). If we were to take an abdominal radiograph as an example, improper collimation affects the QA score to varying degrees based on the patient, clinical indication, and anatomic region of interest. If the patient is an elderly male patient presenting with acute abdominal pain and the presumptive diagnosis of pnemoperitoneum (free air), then excessive collimation of the upper abdomen precludes diagnosis and renders the exam non-diagnostic (QA score "1"). If the same image is in an elderly male patient with renal colic and questionable kidney stones, then the anatomic area of concern is not adversely affected by the excessive collimation and the entire area of interest is included in the image obtained. As a result, this similar image (but in a completely different clinical scenario) would receive a QA score of "3" (diagnostic).

In another example, a young female (age 18) with renal colic sent for an abdominal radiograph to evaluate kidney stones, would have an image taken in a similar manner to the previous examples, with the uppermost portion of the abdomen excluded, but visualizing the kidneys in their entirety. However, while the clinical indication is similar, the patient profile is different. A young female of child bearing age would warrant increased collimation to minimize radiation exposure to the pelvis and gynecologic organs. The lack of collimation has therefore exposed the patient to unnecessarily large amount of radiation which is a safety concern, which must also be factored into the QA analysis. As a result, the QA collimation score is "2" (limited), but does not require the image to be retaken since the anatomic region of interest and clinical indication were adequately evaluated.

In one embodiment consistent with the present invention, computerized pattern recognition (see step S506) could be used to resolve the problem of the human body being, by definition, symmetrical. If one half of the anatomic region of interest is not visualized in its entirety, then the computer program 110 could easily identify the missing anatomy and alert the technologist by display or alarm, as to the specific area not visualized (see step S509). This is a common problem for radiographic and mammographic studies, resulting in "cut off" of the axilla on the mediolateral mammographic image and costophrenic angle on frontal chest radiographs. This relatively simple deficiency is a common cause of retakes and can be easily ameliorated with use of computerized pattern recognition software to compensate for it.

6) Supporting Data

Finally, the last technical variable is supporting data, which is an extremely important, yet overlooked, QA variable. The previous examples have illustrated the clinical importance of supporting data to QA analysis, in addition to interpretation. Patient demographics, pertinent laboratory and clinical testing data, history and physical exam findings, and clinical indication are all essential components in medical image optimization. All components of the QA imaging cycle are affected by this supporting data including the exam selection, defining the optimum acquisition protocol, post-image processing, and interpretation. While insufficient supporting data will not directly require the image to be repeated, it may require the performance of an additional imaging exam.

In one example, three patients are referred for skull radiographs, all in the setting of trauma. The first is an otherwise healthy 35 year-old male without pre-existing medical history who tripped and struck his forehead, and incurred minimal soft tissue swelling with no loss of consciousness. The second patient is a 70-year old male with a history of repeated falls, who is currently taking anti-coagulation medication (i.e., "blood thinners") due to past history of deep venous thrombosis (i.e., blood clot). The third patient is a 6 year-old male with no significant past medical history, but presents with several unusual bruises on his extremities and torso.

If this supporting data was available prior to performance of these requested skull radiographs, two of the requested studies would be changed. The requested skull radiographs to evaluate the first patient (healthy 35-year old male) would be sufficient (assuming the exam is normal). Appropriate imaging evaluation of the second patient (70-year old male with repetitive trauma on anti-coagulation therapy), would consist of CT in lieu of plain radiographs. This is because this patient is at increased risk for intracerebral hemorrhage, which would not be visualized with the requested skull radiographs. In fact, a "negative" skull radiograph report would create a situation of false security and potentially place the patient's life at risk. The third case (6 year-old male with suspected non-accidental trauma) would be concerning for child abuse and warrant a complete bone survey for appropriate diagnosis. Skull radiographs alone would be insufficient for proper diagnosis.

The addition or deletion of this supporting data is clearly important in medical image management and diagnosis, and in the calculation of the QA score (see FIG. 2A, step S511). Thus, the supporting data should be entered into the computer database, and this data can be automatically retrieved by the computer when the image is taken of the patient. Thus, the supporting data is incorporated into the QA analysis and scoring (see steps S501, 521), and feedback on the supporting data can be displayed by the computer program 110 (see step S523) for the benefit of both the referring clinicians and radiologists to improve clinical outcomes. Further, at the same time, supporting data from the computer or EMR can be automatically retrieved for each patient by the computer program 110, and the requested imaging exam can be based on defined protocols and trending analysis (see step S522).

Scoring

The data obtained during the imaging study is also deposited into the computerized QA database where it is stored for prospective and retrospective trending analysis, so as to identify immediate and recurrent problems, as they relate to equipment, personnel, data input, and overall workflow. The result of this automated technical QA analysis is that an automated and unbiased reject/retake analysis is created that is no longer subject to human error and subjectivity.

During the image taking process, any variable which is determined to have a deficiency that exceeds a pre-determined QA standard threshold prestored in the database of the computer (see steps S513, S514, S519), will trigger the computer program 110 to have an alarm, or an electronic message instantaneously sent to the technologist alerting them as to the specific type of deficiency and requirement for correction (see steps S515, S516).

For example, a chest radiographic image with motion rendering the exam non-diagnostic (QA score of "1"), would have an instantaneous message sent in parallel to the console of the CR/DR image acquisition device, the chief technologist's QA worklist, and the comprehensive QA database 113. If a repeat image is not resubmitted to the PACS within a defined period of time (e.g., 5 minutes), an urgent text message is sent to the radiology administrator notifying them of the oversight (see step S515). These "lack of resubmissions" are documented in a separate QA database for continued monitoring and analysis (see steps S517 and S518).

In addition, the individual technical variable scores are automatically tallied and recorded in the QA database (see FIG. 2B, step S520). These can be cross-referenced by the computer program 110 to a number of independent variables including the exam type, patient characteristics, modality, equipment, day/time of exam for trending analysis (see steps S521 and S522).

In one embodiment, the technical acquisition parameters obtained by the computer program 110 during the taking of the radiographic image, can be stored with the medical imaging file in the DICOM header (i.e., computer database 113) for future retrieval and QA review, analysis, and future use (in follow-up exams).

In another embodiment consistent with the present invention, these technical acquisition parameters can be correlated automatically by the computer program 110, with calculated QMDI's and technologist profiles (individual and group) to provide educational and training feedback (see step S523). Specifically, the technologist profile may include, for example, the type of position, the type of radiographic images taken, and a percentage of images taken with a high/low Likert score, etc. The computer program 110 would keep tally of the Likert scores obtained with respect to a particular technologist or group, and if a particular technologist takes images which are consistently low in Likert scores (i.e., the percentage of low Likert scores is high), then training for that technologist may be necessary.

In another embodiment consistent with the present invention, the technical acquisition parameters, may be profiled by the computer program 110, with the best QA scores (for each modality, anatomic region, and individual patient, for example), and the technical acquisition profile can be automatically displayed by the computer program 110 to the technologist as the standard default (see steps S505, S601) prior to performing the next exam on that same patient. This should theoretically improve image quality, interpretation accuracy, and patient safety (by minimizing radiation dose with repeat and additional images).

With respect to another embodiment consistent with the present invention, the computer program 110 can perform prospective outcomes analysis by correlating existing mammography statistics (i.e., true positives, true negatives, false positives, and false negatives) obtained from the imaging, with stored pathology reports, follow-up imaging exams, and QMDIs. The prospective outcome analysis (see steps S521, S522, S523) should provide the means to document a direct cause and effect relationship between improved QA measures (e.g., motion) with diagnostic accuracy, economics, and clinical outcomes.

This electronic QA database 113 can be accessed at any time by the individual technologist, supervisory technologist, department/hospital administrator, or chief radiologist to review individual and collective performance of technologists, technology (e.g., CR devices), and exam types. The trending analysis provided by this data can in turn be used for educational purposes, performance review, and new technology deployment (see step S522).

Thus, based on the cumulative data of these technical QA variables, an overall technical QA score is calculated (see step S511) and recorded by the computer program 110, into the QA database for trending analysis (see steps S520, 522). The trending analysis is performed automatically by the software program 110, which can be customized to the specific needs and concerns of the department (see step S522). This data can also be pooled to provide objective and reproducible comparison data with other imaging departments with similar technology, patient, and clinical profiles (see step S523). These national data can in turn be used to acknowledge those centers of excellence which demonstrate high levels of QA proficiency and continued quality improvement (see step S526).

As stated above, a reject-retake analysis is also calculated to determine the frequency of image rejections and required retakes as it relates to each individual technologist and the collective group (see step S513). The reject/retake analysis is automatically calculated by the computer program 110, from the computer-derived QA scores and analysis (see step S513). Any exam which has exceeded the pre-defined QA threshold calling for the image to be repeated would be tallied as a "reject/retake". The corresponding data associated with this rejected image (e.g., technologist, day/time of exam, equipment used, exposure parameters, location, patient profile, clinical indication, etc.), would be recorded by the computer program 110, to provide future insight as to deficiencies that can be monitored and improved upon in the future (see step S520). This provides important feedback for educational and training purposes, for ongoing quality improvement efforts.

A few relevant examples to illustrate these technical QA variable scores are as follows:

One of the most common medical imaging studies performed is the chest radiograph, which provides diagnostic information about a number of important anatomic structures within the thorax, as well as a large number of clinical entities. The anatomic structures included in a chest radiograph include (but are not limited to) the bony skeleton (ribs, sternum, spine), chest wall, heart, pulmonary and great vessels (aorta, superior vena cava), lung fields, pleura, hila and mediastinum, and upper abdomen. The clinical entities that can be evaluated include a number of different pathologic states associated with each of these anatomic structures, along with evaluation of inserted man-made devices such as a cardiac pacemaker, thoracostomy tube, or central venous catheter.

In our example, we will evaluate QA scoring for two postoperative patients, with respiratory distress, and concern for underlying pneumonia.

Similar analyses and differences in QA scoring can be illustrated for the other technical QA variables, using chest radiography as the imaging study. Positioning expectations for the portable ICU and standing chest radiographic images are far different. Due to differences in magnification, technique, and ability to manually adjust each patient, significant QA scoring differences exist for these two examinations. A portable ICU chest radiograph will commonly limit complete visualization of the chest wall and upper abdomen. For the clinical indication of "cough, rule out pneumonia", this is not a clinically significant compromise for the areas of clinical concern (i.e., lung fields) are visualized in their entirety and would therefore receive a QA positioning score of "3" (diagnostic). If, this same portable chest radiograph had a different clinical indication of "trauma, rule out rib fracture", the QA positioning score would be change from a "3" (diagnostic) to "2" (limited). This is because the primary area of clinical concern (ribs) is part of the chest wall, which was incompletely visualized. Depending upon the degree of chest wall visualization and specific area of symptomatology, this QA positioning score could be further downgraded to a "1" (non-diagnostic). If for example, the area of chest wall that was partially obscured is contralateral to the area of clinical concern, the QA positioning score would be "2" (limited), since the primary clinical question can still be answered. If on the other hand, the area of partially obscured chest wall corresponds directly to the anatomic region of clinical concern, the QA score becomes a "1" (non-diagnostic) due to the inability to accurately detect the presence or absence of rib fracture. This illustrates the fact that QA scoring is dependent upon multiple variables including the technical deficiency, patient profile, clinical indication, and technique employed.

B. Radiologist QA Data

The single most important component of radiologist QA data recorded into the QA database 113 is subjective measures of image quality, which are reported for each imaging exam interpreted as part of the routine workflow using PACS 30. For each exam reviewed, a radiologist is prompted by the computer program 110 by means of a pop-up menu, for example, which requires the radiologist to provide the following data:

1) Overall subjective image quality scale
   1—Non-diagnostic
   2—Limited
   3—Diagnostic
   4—Good
   5—Exemplary For exams with a reported image quality score of ≤2, a mandatory field is required to identify the limiting factor/s, as follows:
   1—Motion
   2—Positioning/Collimation
   3—Exposure
   4—Artifacts
   5—Image Processing
   6—Protocol Employed
   7—Supporting Data
   8—Other (Explain) _____

2) Clinical efficacy (appropriateness) of exam performed
   1—Appropriate based on clinical indication provided
   2—Uncertain, due to insufficient clinical information
   3—Inappropriate, exam deemed unnecessary
   4—Inappropriate, alternative imaging study preferred (Specify Preferred Imaging Exam _____)

In addition, radiologist and exam-specific data is recorded by manual entry and by the computer program 110, respectively, into the QA database 113 to include the specific types of image processing utilized, image manipulation (e.g., window/level adjustment, multi-planar reconstruction), and supporting patient demographic, imaging, and clinical data accessed from the RIS 20, PACS 30, and EMR. These data are recorded as a function of the individual radiologist, exam type (anatomic region and modality), clinical indication, and patient profile. It provides valuable information that can be cross-referenced by the computer program 110 with clinical outcome data (in the forms of discharge diagnosis, operative/procedure notes, pathology reports, etc.) to determine which data points (and radiologist profiles) are most informative and accurate in achieving diagnostic accuracy. These data can in turn be directly embedded into radiologist workflow by the computer program 110 (see FIG. 4, step S708), so that each radiologist's profile is quantified and "best practice" templates are created based on the exam type, clinical indication, and individual radiologist preferences (see step S709).

Pertinent examples of how this strategy would be employed are as follows:

In one example, a radiologist is reviewing a brain MRI with the clinical indication of acute onset of right arm weakness. Based on the established image acquisition and interpretation protocols for "stroke", the radiologist is presented with conventional spin echo sequences in orthogonal planes, supplemented by specialized diffusion and perfusion images, and MR angiography (see steps S700, S701). The individual radiologist has an identified preferred display hanging protocol using a 4 on 1 format, with axial spin echo and diffusion images displayed by the computer program 110, side by side on the left hand monitor and historical comparison CT and MRI examinations displayed on the right hand monitor, with comparable MRI sequences anatomically linked.

Window/level settings are automatically adjusted by the computer program 110, to the radiologist's preferences (see step S702) with reconstructed MR angiographic images displayed in axial and coronal planes. The patient's medical, laboratory, and imaging files are automatically queried (using artificial intelligence techniques) by the computer program 110, to provide the radiologist with a synopsis of the patient's past medical and surgical history (which includes a prior right carotid endarterectomy and old right hemispheric infarct), outside report of cerebral angiography, and recent transcranial ultrasound (see steps S700, 701).

An example of how this might apply to a chest radiographic image, would be two radiologists—A and B—who have different preferences for the exposure of the image. The radiologists would be independently reviewing the same standing chest radiographic image on a patient with a longstanding smoking history being screened for lung cancer. Radiologist A would prefer his/her image to be slightly under-penetrated (i.e., lighter), while radiologist B would prefer his/her image to appear more over-penetrated (i.e., darker). When the radiologist name or identification number etc., is inputted into the computer system 101 at the start of the image taking process, the program 110 would automatically search its database 113 for predefined user-specific preferences, such as preference for exposure (see step S600). Thus, after the image is taken, the computer would automatically apply the predefined preferences in post-processing to the image (i.e., by adjusting the look up table), and each image can be displayed independently by the program 110, providing each user with the idealized "look and feel" that they desire (see step S702). In each case, the technologist-selected image acquisition parameters are the same, but the appearance of the image when displayed for interpretation by the program 110, varies for each individual radiologist. While these post-processing techniques will not alter the computer-generated technical exposure QA score, it would allow for enhancement of category "2" (limited) images, which may obviate the need for repeating the image.

In another example, another radiologist is reviewing a chest radiographic examination with the clinical indication "shortness of breath" (see steps S700, S701). Based on the specific radiologist's profile (see step S702), the images are automatically processed by the computer program 110, and displayed for the radiologist for review (see step S703). Additional history obtained from the EMR, when queried by the user, and prior imaging report archives, relate a previous diagnosis of chronic interstitial lung disease (see step S704). The corresponding CT exam is automatically retrieved by the program 110, from the patient's electronic imaging folder and pre-selected "key images" chosen by the computer program 110 (see step S704), are displayed alongside the chest radiographic images to be interpreted. Based on this additional history of "interstitial lung disease", the computer program 110 automatically applies a specialized image processing algorithm (edge enhancement) to highlight the interstitial lung disease, and displays both the "standard default" and "processed" images next to one another for review by the user.

In another example, a radiologist interpreting a screening digital mammogram in a high-risk patient (history of maternal breast cancer) has the images displayed in the customary fashion, with side by side comparisons of current and historical comparison images. Based on the "best practice" template (see step S709), the computer program 110 automatically provides a computer-aided diagnosis (CAD) overlay (see step S710), which the radiologist can turn on and off using the input means 104. When the CAD program 110 identifies a focal area of suspicious microcalcifications, the computer program 110 automatically magnifies this area on both the current and historical comparison studies, allowing for temporal comparison at a higher resolution. The radiologist reports this as a BIRADS category 4 (suspicious for malignancy) in the database 113 and issues a stat report to the referring clinician with recommendation for surgical biopsy (see step S711). An electronic message is simultaneously sent by the computer program 110, to automatically retrieve the surgical pathology report at the time of recommended biopsy and link the mammography and pathology reports for direct correlation (see step S712).

C. Vendor QA Data

In order to automate the overall medical imaging QA process, it is imperative that routine quality control (QC) be employed on the acquisition and display devices. This can be done through the use of QC phantoms which are directly embedded into technologist and radiologist workflow to ensure that quality assurance is maintained at the points of image acquisition, display, and interpretation.

A Quality Control (QC) phantom 32 for digital radiography is a device constructed from sheets of copper, aluminum, acrylic, and other attenuators, with embedded resolution test patterns, step wedges, and fiducial markers that provide a means to measure and verify the performance characteristics of the x-ray system and x-ray detector (both 21). The phantom 32 may be part of the vendor's components to test system-specific characteristics, or may be a "third-party" phantom to measure and verify system-independent performance characteristics. A good QC phantom "system" provides an object that is conducive to easy handling and positioning, allows the use of typical x-ray acquisition technique factors for common imaging procedures, requires only one or two x-ray image acquisitions with minimal user interaction, uses a computer program 110 to analyze phantom images with automatic software algorithms, log data results, plot trends and alert the user when the system is outside of tolerance limits.

System performance measurements within the QC phantom 32 include but are not limited to the following:

Spatial resolution assessment using a computer program 110 to perform qualitative evaluation of bar phantoms or quantitative evaluation of an edge spread or line spread tool to generate a modulation transfer function (MTF) in the center of the image as well as peripheral areas. Acquisition of data with magnification addresses geometric blurring by the focal spot.

Contrast resolution assessment using a computer program 110 to perform qualitative evaluation of decreasing diameter and decreasing thickness disk attenuators (contrast-detail section), quantitative measurement of contrast to noise ratio using automated region-of-interest (ROI) analysis.

Dynamic range measurement and system exposure linearity response is performed by a computer program 110 using a calibrated plastic step wedge phantom projection with ROI measurements. This demonstrates the capabilities of the detector 32 to capture a wide range of exposures.

Distance measurement accuracy and detector element size calibration verification using the fiducial marker image projections of a known distance (for a given magnification factor) in horizontal, vertical and oblique directions in the image, is performed using a computer program 110.

Peak kilovolt (kVp) assessment is performed by a computer program 110, using differential transmission measurements through copper filter thicknesses; half-value-layer (HVL) determination from evaluation of aluminum step wedge transmission signals.

Image uniformity and signal to noise ratio (SNR) evaluation of a "for processing" image is performed by a computer program 110 using ROI analysis of central and peripheral values of a uniformly exposed constant thickness object, and verification of flat-field correction algorithms using noise power spectrum (NPS) quantitative algorithms.

Artifact evaluation/analysis tests performed by the computer program 110, employ uniformity images in 6) above, for evaluation. In particular, bad detector element mapping, column and row defects before flat-field correction, image retention artifacts, etc. are evaluated by the computer program 110, using algorithms to seek high and low value pixel defects, clumps, vertical and horizontal lines, and all signals above or below a threshold level in the image.

Each test (1-7) is automatically performed by the computer program 110 (see FIG. 5, step S800) on the image data, logged and stored with respect to the date of acquisition. All QC image data is achieved in the "for-processing" format by the computer program 110, for qualitative and quantitative re-evaluation when necessary. Immediate feedback to the technologist is provided by the computer program 110, on the image review workstation as a color-coded response of green (acceptable, ready for patient imaging)—yellow (patients can be imaged, but attention to system calibration/repair is needed)—or, red (equipment MUST be repaired prior to patient imaging) for each of the phantom subsections. An overall green-yellow-red is also displayed, with 2 or more yellow warnings eliciting an overall red (or whatever is deemed appropriate) (see step S802).

In addition to the automatic feedback, the computer program 110 can store and use more detailed information of trend analysis of the measured parameters for the prediction of detector 32 or other system failures before they occur, allowing preventative maintenance repairs before the system becomes inoperable (see FIG. 2B, steps S522, 523).

In one embodiment, depending on the specific system, the exposure index calibration can also be performed by the computer program 110 (see step S802), using known incident exposures to the detector 32 and verifying the exposure index value accuracy reported by the digital detector 32. As this exposure reporting value is currently vendor specific, an algorithm adjusted to the vendor's methodology used by the computer program 110, can provide a means to determine the accuracy of the reported values, and an ability to give feedback information to adjust the exposure index accuracy of the digital imaging system (see step S803).

The exposure index represents a value proportional to the overall incident exposure to the detector 32, and therefore to the signal to noise ratio (SNR) and to image quality. However, a need to keep the radiation dose as low as reasonably achievable to the patient pushes the detector exposure to lower values. Optimization attempts to achieve appropriate "disease-specific" image quality at the lowest patient dose possible. Since the SNR is proportional to the square root of the detected exposure measured by the detector 32 (assuming quantum noise limited operation), then the SNR is proportional to the detected exposure and related to the exposure index. In many digital detectors 32 with interfaces to x-ray generators, the kVp (0018,0060), mA (018,1151), and exposure time (0018,1150) parameters are mapped to DICOM (tag, element) header values, as well as the geometry of the x-ray system (source to image distance and object to image distance). This information can be extracted by the computer program 110 to calculate a value related to patient dose, and by calculating the SNR/patient dose, provides a unitless "figure of merit" (FOM) that can aide in the optimization of specific imaging procedures and determination of appropriate radiographic techniques (selection of kVp to maximize the FOM for the lowest possible detector exposure) (see step S607).

Additionally, because digital detectors 32 have a wide dynamic range and are very forgiving, particularly when overexposures occur (the images look good, but the patient dose is too high), the exposure index generated by the computer program 110 can provide feedback to the technologist to avoid a "dose-creep" problem. Extreme overexposures will lead to signal saturation and a loss of information in over-penetrated areas of the image. Underexposures are also a problem, because the images are too noisy for the intended diagnostic need. Both the exposure index (proportional to SNR) and FOM values can be used by the computer program 110 to generate feedback not only to the technologist, but to technologist administrators and to radiologists for tracking down image problems and to provide continuous quality improvement and better patient care (see step S523).

For both the technologist and the radiologist, the soft-copy display quality and viewing conditions are extremely important. The QC phantom 32 and software program 110 contains test images that verify qualitative and quantitative image information transfer to the human view independent of the quality of the images generated from a digital radiography system. A common test image phantom is the SMPTE test pattern, which drives the display system to the low-end dark and to the high-end bright ranges. Within the extreme dark and bright areas are inset boxes of 5% higher and lower digital values, respectively, to test the ability of the display and video driver to appropriately render the information visible. This quick qualitative check by the computer program 110, determines whether the digital driving levels of the video card are set properly; if not, calibration using the DICOM part 14 Grayscale Standard Display Function (GSDF) should be performed, and the test re-evaluated.

Additional areas in the image test performed by the computer program 110, display uniformity, linearity, spatial resolution, and distortion by providing a uniformly bright area, variations in brightness intensity in linear steps from dark to bright, high contrast and low contrast test patterns to demonstrate spatial resolution capabilities of the monitor, and a standardized grid pattern to test geometric distortion of the display.

D. Clinician QA Data

An important and often overlooked component of any imaging QA program 110 is the evaluation of imaging utilization, specifically as it relates to established appropriateness criteria. Over-utilization not only results in excessive cost but also has the potential to adversely affect patient safety, due to the additional radiation exposure and potential complications inherent to these inappropriate and unnecessary exams. Complications can take a number of forms including contrast extravasation, allergic reaction to contrast administration, and physical injury to the patient (which is particularly common in the course of interventional procedures).

Utilization review by the clinician can be partly automated by accessing the QA database 113 for radiologist assessment of clinical efficacy (as previously described), as well as cross-referencing the clinical indication and patient history (which are contained within the EMR) with established imaging criteria for appropriateness, which is currently available in existing computerized physician order entry (CPOE) programs, to generate reports (see step S706) which are stored in the database 113 (see step S707).

These CPOE programs also require adequate clinical input at the time of exam ordering, thereby assisting the imaging QA process. The comprehensive data contained within the QA database 113 can in turn be used to generate reports for clinician education and training, to ensure that imaging utilization is appropriate (see step S523). Clinician profiles can be generated by the computer program 110, that identify those types of exams or specific physicians that tend to misappropriate imaging services.

E. Patient QA Data

Despite all of the attention and scrutiny placed on patient safety, few safeguards currently exist within most medical imaging departments to document and analyze potential adverse outcomes, as they relate to medical imaging. If for example, a patient was to incur an allergic reaction to intravenous contrast administration, there is no reproducible method within the RIS 20 or PACS 30 that reproducibility alerts radiology personnel prior to future studies. This is particularly troublesome in the environment when patients often seek medical services at different institutions and often provide incomplete histories.

In the present invention, the imaging QA database 113 provides the means with which to document all relevant medical history that may serve to alter medical imaging delivery.

This can take a number of different forms including contraindications to specific imaging studies (e.g., cardiac pacemaker for MRI), previous allergic reactions to medications or contrast agents, or medical conditions that preclude administration of iodinated contrast (e.g., renal insufficiency) (see step S501).

As previously mentioned, one of the most commonly overlooked areas of patient safety that can be prospectively improved upon is the radiation exposure experienced with imaging exams that utilize ionizing radiation. By tailoring the exam type and protocol to the specific patient and the clinical indication, radiation can be effectively reduced without compromising exam quality. The imaging QA database 113 can record numerous data points to facilitate this radiation dose optimization including:

Exposure parameters (and calculated radiation dose) for each individual exam;

Cumulative radiation exposure for each patient;

Previous imaging exams' exposure parameters and the corresponding image quality scores (this provides optimum exposure parameters and reduces the need for retakes); and Clinical indication and past medical history which allows for tailored dose reduction protocols, specific to the clinical question at hand.

F. Administrative QA Data

The compilation of data contained within the imaging QA database 113 provides the means for supervisory and administrative staff to use the computer to generate reports so that they can systematically review the various profiles on technologists, radiologists, clinicians, and technology. By performing trending analysis on this data (see step S523) using the computer program 110, administrators can develop a better understanding of how imaging department services and practitioners can improve QA and the existing limitations.

These QA profiles encompass a number of predetermined stakeholders and perspectives and include technical deficiencies in image acquisition, safety concerns inherent to ionizing radiation, physician compliance (as it relates to both radiologists and referring clinicians) and technology concerns relating to image acquisition devices, technology integration, and software used in the overall QA process.

Personnel performance is an important component of the automated QA program 110 and is intended for educational and training purposes, in order to facilitate improved workflow and end-quality (see step S523). For the technologist (who is the sole individual responsible for image acquisition), performance evaluation consists of a number of measurements including (but not limited to) the following:

Specific protocols used (as it relates to the clinical indication, technology used, patient profile, and supporting clinical data).

Exposure parameters (as it relates to the patient profile, technology, and clinical indication. In this particular situation, the patient profile consists of physical characteristics (e.g. body habitus), clinical status (e.g., ambulatory versus non-ambulatory), and radiation profile (e.g., cumulative radiation exposure).

Exam-specific QA characteristics (which are specific to the anatomic region surveyed, imaging modality used, and clinical indication.

One example of exam-specific QA characteristics would be a pediatric elbow radiographic exam performed to evaluate trauma. In this particular patient population, the identification of a non-displaced fracture is often dependent upon the indirect radiographic sign of fat pad displacement, as opposed to direct visualization of a fracture. In order to optimize detection of a non-displaced fracture in this specific type of exam, a properly positioned true lateral view is mandatory. Improper positioning results in inaccurate detection of the fat pads, which in turn can lead to erroneous diagnosis.

4) Overall subjective image quality, as judged by the interpreting radiologists and clinicians.

This image quality score is not intended to be a "beauty contest" or facsimile to the standard film image, but instead a measure of the imaging examination's ability to detect pertinent pathology. In addition to the comprehensive image quality score, physicians would be prompted by the computer program 110, to provide the specific variables that limit overall quality in the event of a "low" image quality score (as previously discussed).

Physician compliance data (for both radiologists and referring clinicians) would also be an important component of the administrative QA data review. This data would record (and provide a physician-specific and group profiles) a number of important variables that contribute to medical imaging QA such as:

Physician compliance to image quality scoring and identification of deficiencies;

Physician education and consultation (as it relates to ordering, decision support and communication) of medical imaging studies. For the radiologist this may entail documentation of results reporting of emergent or clinically unexpected findings. For the clinician, this may entail electronic auditing (and documentation) of on-line education, review of imaging data, and recording of clinically relevant information to supplement exam ordering and interpretation. This would also include documentation of patient consultations (by both clinicians and radiologists) as it relates to safety concerns.

3) Utilization review (in conjunction with data obtained from the CPOE system), that allows for analysis of the appropriateness of exam ordering and the timely delivery of imaging services;

4) Physician compliance to QA standards and regulatory policies. This can take the form of institution-specific, community-wide, and governmental QA regulations. Examples of existing policies that oversee QA include HIPAA, JCAHO, and MQSA.

Technology/vendor issues include those hardware and software entities that are responsible for the various steps in the medical image chain including acquisition, processing, transmission, storage, display, interpretation, and reporting. Preventative maintenance and service logs, software upgrades, and equipment downtime are all incorporated into this component of the administrative QA record. Integrating the aforementioned technical and clinical QA data using the computer program 110, into institutional information systems also requires integration of the imaging modalities with PACS 30, RIS 20, HIS 20, and EMR. Existing industry-wide standards (HL-7, IHE, DICOM) currently exist to define these standards and track industry compliance.

In addition, "digital dashboards" are commercially available software programs that allow the administrator to continuously monitor and survey departmental workflow and equipment malfunction (see FIG. 2B, step S524), which in essence creates an ongoing technology QA log. While the various components required for this comprehensive administrative QA program 110 exist (in one form or another), no entity to date has integrated these disparate data points into a single, all inclusive system for automating QA surveillance, as in the present invention.

In operation, the present invention includes the following steps as shown in the FIGS. 1-4. However, it would be well known to one of ordinary skill in the art that the steps may be combined, carried out simultaneously, carried out alternatively, or carried out in a different order, or with the omission of some steps, or in difference sequences, as long as the intent of the present invention is carried out.

Accordingly, in the method of the present invention, the radiologist turns on the client computer system 101, which may be a stand-alone PC, or part of or connected to a client workstation known in the radiological field as the PACS workstation 30. In this exemplary embodiment, the client computer 101 is the PACS 30, and some or all of the present invention, with respect to imaging display device 102, computer memory 109 and program 110 etc., is contained within the PACS 30 instead of being provided separately.

Thus, the user logs onto the PACS system 30 once the client 101 is operational.

The computer program 110 will then offer the user a menu directed to imaging studies which the technologist can then select, and the program 110 will open up in the worklist folder listing image files available for analysis, from the menu offered (see FIG. 2A—step 500).

The radiologist can select and the computer program 110 will select a new imaging study, or can also load a previous imaging study (i.e., patient data), including but not limited to image data corresponding to radiological examinations of patients from the PACS 30, and additional supporting information, including but not limited to laboratory data, pathology reports from the Electronic Medical Record (EMR), patient demographics, administrative QA information, clinician and radiologist profile information, etc., from data storage 113, onto the display 102. Note that the PACS 30 stores information according to existing standards such as DICOM. The data from the PACS 30 is stored in an examination image storage device 113 for example, where it can be accessed via the client computer 101 for display on the image displaying device 102. Alternatively, the quality assurance system 100 of the present invention can directly access the PACS images in storage 114 without the need for an intermediate storage device 113, for example.

The selected imaging study—including all of the associated unread (or read) examination files for that patient, if any—is displayed by the computer program 110 on the display 102 of the client 101 in step S501. The study can be organized by the computer program 110 by DICOM series prior to display.

When the study only contains a few images (radiography or mammography), the radiologist reviews the images in a static fashion. If the imaging study contains many images (CT, MRI), the images are reviewed in a dynamic fashion using a cine format (which is akin to a movie where the images rapidly scroll up and down in a sequential fashion).

In step S502, the patient is hooked up to any of the devices 23, 24, 31, 32 associated with obtaining a radiographic image, and positioned for taking the radiographic image. In step S02, the technical variables input which collect data from the patient and the radiographic device 21, is received from sensors 23, phantom devices 24, reflective devices 31, and QC phantoms 32 (if any or all are present).

With respect to the issues of motion and positioning, the method of the present invention includes generating QMDI scores from the motion sensors 23, phantom devices 24, and reflective devices 31, in step S503. Once the QMDI scores are generated, a QA score is calculated based on the input from these devices in step S504.

In an another embodiment, the computer program 110 may retrieve an ideal examination imaging study from the database 113 (step S505), and perform a comparison and analysis of the images to determine if there have been any changes in positioning or any issues of collimation (step S506).

Using this analysis, a positional and collimation score can be determined by the program 110 is step S507. If a change needs to be made in the position of the patient due to the score (S508), the program 110 will notify the user in a display, message or alarm (step S509). In that event, the technologist will change the position of the patient and then the new input from the sensors 23, 24, 31 will be received to restart the comparison/analysis process of steps S502, and S505-507.

If the position and collimation score is acceptable according to the predefined limits in the database 113, as determined by the computer program 110, then the QA score is calculated based on the technical variables inputted into the system 101 (step S504).

Based upon the QA score calculated from the motion sensors 23, 24, 31 etc., the program 110 can determine whether to recommend further changes to the technical variables (i.e., motion sensors 23, 24, 31), or position of the patient etc. (step S510). As stated above, this would entail the technologist changing the position of the patient or the position of the sensors 23, 24, 31, which will result in new input being received in step S502.

After the imaging study has been taken, the QA score is calculated by the program 110 (step S511) using information/supporting data etc., retrieved from the database 113 (step S512).

The QA score that is calculated, undergoes a reject/retake analysis (step S513). If the technical variables exceed a certain threshold, and/or if the QA score is 1 or 2, that means that there is an issue with the imaging study, such as with the position, motion, collimation, etc. (step S514), and the program 110 will transmit a warning to the user et al., in step S515, to discard the image, correct the problem and repeat the imaging study (step S516).

If the imaging study is not retaken within a certain period of time (step S517), then this error is stored for future trending analysis (step S518), and another warning transmitted (step S515) until the imaging study is retaken (step S517) and the process restarted.

If the QA score is 3 or 4 (step S519), then the imaging study need not be performed again, the examination is completed. The QA score is then stored in the database 113 (see FIG. 2B—step S520), and is correlated with other QA information in the QA database 113, such that an analysis of the imaging study (step S521), as well as a trending analysis (step S522) are performed.

This analysis is displayed in step S523 and recommendations for education, and feedback, are presented to the user. In addition, the program 110 will perform monitoring and analysis of QA issues and more generally, department workflow and QA (step S524).

QA data obtained from the analysis is also pooled with other imaging departments (step S525) and cross-referenced/analyzed, along with the results of the monitoring and analysis of those departments (step S524), to result in recommendations for education and provide feedback to those users and the departments (S526).

Along with the emphasis on the technical variables related to motion, position and collimation, FIG. 3 discloses the steps of the method of the present invention with respect to exposure parameters and the resolution of artifacts in imaging studies. The steps in FIG. 3 may be performed concurrently with those in FIG. 2, or separately therefrom, or certain steps can be performed separately or in combination, or omitted.

After opening the file for the imaging study as above in step S500, in one embodiment, the computer program 110 retrieves QA and exposure parameters from the database 113, in order to ascertain the exposure parameters for the individual imaging study (step S600).

In one embodiment, default exposure parameters are set by the program 110 (step S601), which are used during the imaging study. Thereafter, the QA score is calculated based on the technical variables, as in FIG. 2A, step S504 et seq.

In another embodiment, the program 110 has performed an analysis of exposure parameters, and thus, sets predetermined (i.e., unique) exposure parameters (in step S602). Thereafter, the QA score is calculated based on the technical variables, as in FIG. 2A, step S504 et seq.

In another embodiment, the technical variables related to the exposure parameters are received by the program 110 in step S603. However, if the exposure parameters retrieved from the database 113, and the settings for the new imaging study, would bring the cumulative exposure of the patient over a predetermined limit stored in the database 113 (step S604), the technologist would be warned and instructed by the program 110 to use a low dose protocol or an alternative examination (step S605). Thereafter, the QA score is calculated based on the technical variables, as in FIG. 2A, step S504 et seq.

If the cumulative exposure of the patient will not exceed the predetermined limit, then, the technologist may set the exposure parameters such that the program 110 will receive and store those technical variables (step S603).

In one embodiment, a PSNR analysis is also performed (step S606), but this step need not be performed before the radiation dose exposure is calculated in step S607. Once calculated, the exposure parameters are correlated with clinician and patient specific variables in step S608, before a QA score is calculated based on all the technical variables (see FIG. 2A, step S504). Thereafter, the method follows the same sequence as in steps S510 et seq.

In another embodiment, after the exposure parameters (i.e., technical variables) are inputted, the image taken in the study is cloned (step S609), and a shift and subtract operation is performed in step S610. Thereafter, a quantitative analysis, and a noise spectrum analysis are performed, among others, in step S611 to determine a final QA composite image, where any artifacts in the image may be isolated, or overlayed on the image obtained (step S612).

Thereafter, the QA score is calculated based on the technical variables, as in FIG. 2A, step S504 et seq.

Figure 4:
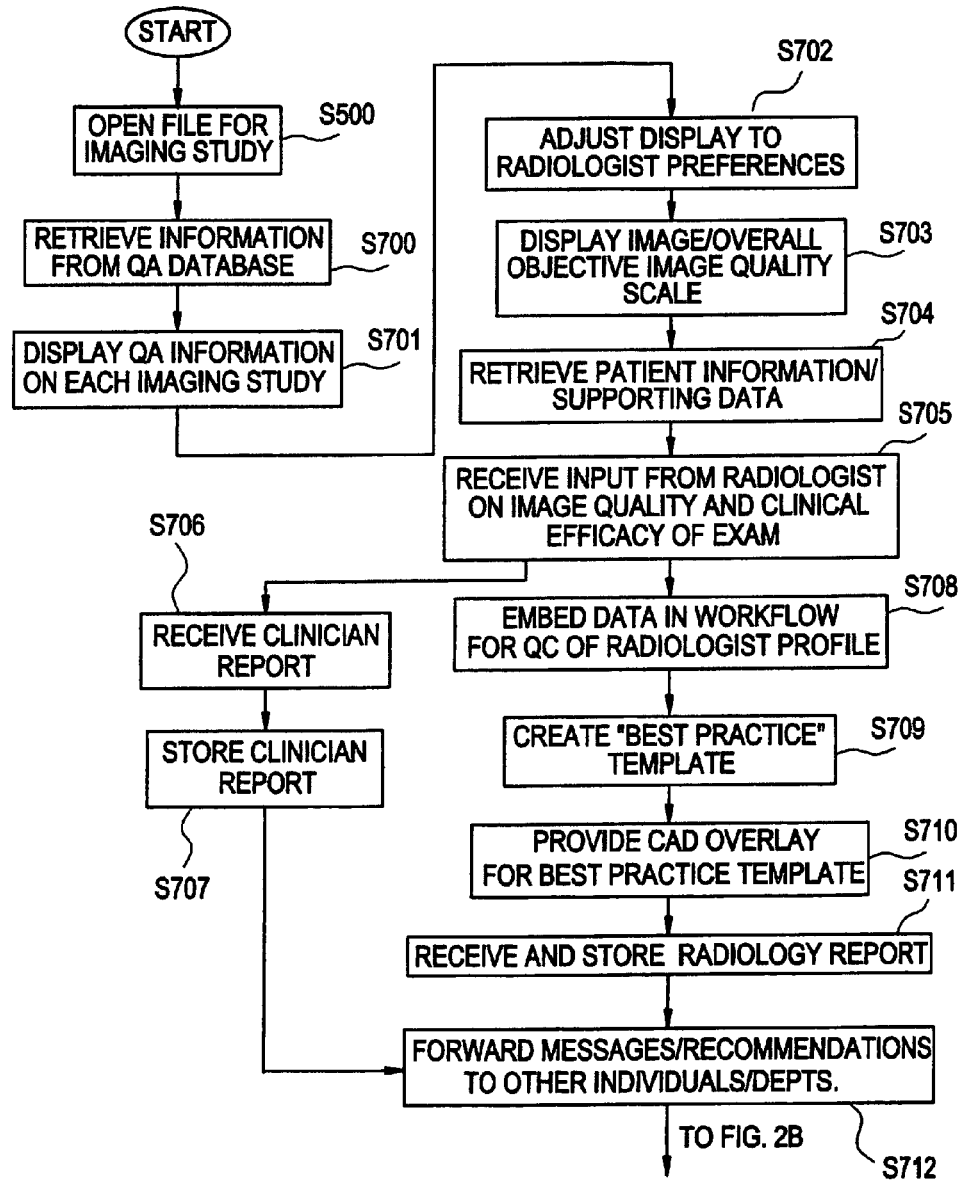
FIG. 4 is a flow chart of a quality assurance system with respect to radiologist and clinician inputs, according to one embodiment consistent with the present invention.

With respect to FIG. 4, the steps involved in the present method of ensuring QA in radiology with respect to radiologists and clinicians, may be performed concurrently with those in FIGS. 2 and 3, or separately therefrom, or certain steps can be performed separately or in combination, or omitted.

The steps include the program 110 retrieving information from the QA database in step S700, after the program 110 opens the file for an imaging study (step S500). QA information on each imaging study is displayed on the monitor 102 by the program (step S701), with the program 110 automatically adjusting the format of the display 102 according to prestored radiologist preferences (step S702). The overall objective image quality scale (i.e., QA scores) are displayed for the user (step S703), and patient information and supporting data are retrieved in step S704 to provide additional information for the radiologist.

Once the radiologist has performed his analysis, he/she will input the findings into the computer 101, on the image quality and clinical efficacy of the image study (step S705). Thereafter, the clinician will review the radiologist's findings (step S706), and the clinician's report will also be stored in the database 113 (step S707).

The radiologist's findings based on the QA scores etc., will be embedded in the workflow for program 110 quality control analysis of the radiologist profile (step S708). The program 110 can utilize the information in the database with respect to each radiologist, and perform a trending analysis to produce a "best practice" template for all radiologists to follow (step S709). This "best practice" template can be provided as a CAD overlay in some embodiments (step S710).

These reports and templates are all stored in the database 113, and messages and feedback are forwarded to other radiologists/clinicians, and departments in step S712. Thereafter, QA scores are calculated based on the technical variables, as in FIG. 2B, step S521 et seq.

Finally, the steps involved in assuring QA of the radiographic equipment 21, include those in FIG. 5. These steps may be performed concurrently with those in FIG. 2, or 3, or 4, or separately therefrom, or certain steps can be performed separately or in combination, or omitted.

The QC phantoms 32 are positioned with respect to the radiographic equipment 21, and the data from the phantoms 32 are received by the program 110 and a plurality of sophisticated testing and analysis of the data is performed (step S800).

Based upon the results of the testing and analysis, the program 110 will display a coded response to the user for calibration and/or repair of the radiographic equipment 21 (step S801).

Further, an exposure index calibration based on the received exposure parameters (see FIG. 3, step S603), is performed by the program 110. The program 110 will then display the recommended adjustment to the equipment 21 based on the exposure index (step S803). Based on the equipment adjustments, the program 110 will calculate the SNR (step S804), and this information, which can be utilized by the program 110 to calculate radiation dose exposure to the patient, is inputted into the technical variables received by the program in step S603 in FIG. 3.

Once the patient radiation dose is calculated (step S607), then feedback is provided to the technologist/radiologist on QC issues with the equipment that affect the imaging study (step S521 (FIG. 2B)), the information stored and a trending analysis performed (step S522), and recommendations provided for education, and feedback provided, to the clinicians, radiologists, and departments (S526).

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A computer-implemented method for quality assurance in radiology, comprising:
    retrieving quality assurance and exposure parameters from a database of a computer system;
    receiving information on technical variables, including radiation exposure parameters, from imaging equipment in the performance of an imaging study on an individual patient, said information which is stored in said database;
    determining, using a processor, whether a cumulative exposure to said individual patient exceeds a predetermined threshold stored in said database; and
    presenting to a user on a display, prior to another imaging study on said individual patient, at least two of the following options: 1) specialized relatively low-dose protocols, 2) imaging examinations without ionizing radiation, or 3) analysis of future imaging examination requests, on condition that said processor determines that said cumulative exposure to said individual patient exceeds said stored predetermined threshold.

2. The method of claim 1, wherein said technical variables include data on patient motion, positioning, radiation exposure, imaging apparatus artifacts, image collimation, and supporting data.

3. The method of claim 2, further comprising:
    recording and storing radiation exposure parameters from imaging studies using said imaging equipment, in said database;
    storing predetermined protocol parameters in said database; and
    cross-referencing, using a processor, said protocol and radiation exposure parameters with clinical data stored in said database, on said individual patient, pertinent to examination indication, laboratory data, and diagnosis, in order to make a comparison and analysis with said imaging studies, to thereby improve diagnostic accuracy and reduce radiation exposure by minimizing additional and unnecessary imaging studies.

4. The method of claim 3, further comprising:
    performing a pre-scan of an anatomic region of said individual patient using said imaging equipment, and storing data from said pre-scan in said database;
    creating a pixel density map of said anatomic region using said data from said pre-scan, and storing said pixel density map in said database;
    performing a histogram analysis of a pixel density of said pixel density map, using a processor, to compute optimum radiation exposure parameters, including both image quality and radiation exposure dose; and
    storing said optimum exposure parameters in said database and utilizing said optimum exposure parameters, using said processor, before said imaging study is repeated, to improve at least image quality.

5. The method of claim 4, further comprising:
    performing an existing peak analysis to noise (PSNR) analysis, using said processor, to evaluate a variability in pixel data to quantitatively measure an amount of noise contained within an image in one of said imaging studies; and
    calculating, using said processor, an inflection point at which a reduction in said radiation dose is achieved without clinically significant degradation in said image quality.

6. The method of claim 5, further comprising:
    correlating, using said processor, said one of said imaging studies with previous imaging studies and examinations and patient information stored in said database.

7. The method of claim 5, further comprising:
    analyzing, using said processor, said pixel density map obtained over said anatomic region in conjunction with said PSNR analysis to produce an automated correction to provide a required diagnostic information at a lowest radiation dose to said patient.

8. The method of claim 7, further comprising:
    performing, using a processor, an analysis of said imaging studies for use in technologist education and training, development of decision support programs, and patient outcomes analysis.

9. The method of claim 8, wherein said decision support programs are customized to end-user preferences, specific clinical indication and a patient anatomy being evaluated, and are automatically displayed by said processor, to a user.

10. The method of claim 7, further comprising:
    calculating a quality assurance score for each of said technical variables along with said supporting data, using said processor;
    wherein said supporting data includes at least patient and examination-specific identifying data for each said imaging study performed.

11. The method of claim 10, further comprising:
    determining, using said processor, whether changes are to be made to said technical variables or said position of said individual patient based on said quality assurance score.

12. The method of claim 11, further comprising:
    providing a reject/retake analysis of said quality assurance score using said processor;
    wherein when said quality assurance score is below a predetermined value, images from said imaging study are discarded by said processor, corrective measures are taken, and said imaging study is repeated; and
    wherein when said quality assurance score is acceptable, said quality assurance score is stored in said database and correlated with other quality assurance information, and a trending analysis performed.

13. The method of claim 12, wherein when said imaging study is not repeated within a predetermined period of time, a warning is transmitted by said processor to said user via electronic means.

14. The method of claim 12, further comprising:
providing recommendations for education and feedback to said user based on said quality assurance information; and
performing monitoring and analysis of quality assurance issues.

15. The method of claim 14, further comprising:
pooling quality assurance information from said database with quality assurance information from other imaging departments, to provide recommendations for education and feedback to other users and said other imaging departments.

16. The method of claim 10, further comprising:
embedding a user's findings on said imaging study based on said quality assurance score, in a workflow of said user, for quality control analysis of a profile of said user;
performing a trending analysis to produce a best practice template for all users; and
recalculating said quality assurance score based on said technical variables.

17. The method of claim 3, further comprising:
setting default radiation exposure parameters for use during said imaging study.

18. The method of claim 3, wherein said radiation exposure parameters are set based on an analysis of said technical variables.

19. The method of claim 3, further comprising:
cloning an image from said imaging study after said radiation exposure parameters are inputted;
performing a shift and subtract operation on said image;
performing a quantitative analysis and a noise spectrum analysis on said image; and
determining a final quality assurance composite image.

20. The method of claim 2, wherein motion is detected by placement of motion phantoms on a patient prior to said imaging study.

21. The method of claim 20, further comprising:
generating, using said processor, a quantitative motion detection index (QMDI) score based on said technical variables including one of movement of a patient, or blurring or contour irregularity of each phantom image, which is superimposed directly over a medical image.

22. The method of claim 21, further comprising:
correlating said QDMI score with variables including an anatomic region being imaged, a modality, patient physical characteristics, and clinical indication, to determine a quality assurance motion score, to determine whether a quantified amount of motion is acceptable relative to each examination type and clinical indication.

23. The method of claim 20, further comprising:
performing testing and analysis on data from said motion phantoms;
displaying a coded response to said user for calibration and/or repair of said imaging equipment based on said analysis;
performing an exposure index calibration based on received radiation exposure parameters from said imaging equipment;
displaying a recommended adjustment to said imaging equipment based on an exposure index;
calculating an SNR based on adjustments to said imaging equipment;
calculating a radiation dose exposure to said individual patient; and
inputting all information on said SNR and said radiation dose exposure calculation into said technical variables.

24. The method of claim 23, further comprising:
providing feedback to said user on quality control issues with said imaging equipment that affect said imaging study;
performing a trending analysis and providing recommendations for education and feedback to users and departments.

25. The method of claim 2, wherein microscopic motion detection sensors are used to provide real-time motion feedback directly to said imaging apparatus.

26. The method of claim 25, wherein reflective devices are used in addition to motion detection sensors, and said processor and said motion sensors process reflected light to determine a magnitude and directionality of said motion.

27. The method of claim 2, further comprising:
correlating, using said processor, said imaging study on said individual patient, with an ideal imaging study from said database, to perform a comparison and analysis of the images to determine changes in positioning or collimation.

28. The method of claim 27, further comprising:
determining, using said processor, a positional and collimation score based on said comparison and analysis, and using said positional and collimation score to determine whether a position of said individual patient should be changed.

29. A computer system for quality assurance in radiology, comprising:
at least one memory which contains at least one program having the steps of:
retrieving quality assurance and exposure parameters from a database of a computer system;
receiving information on technical variables, including radiation exposure parameters, from imaging equipment in the performance of an imaging study on an individual patient, said information which is stored in said database;
determining, using a processor, whether a cumulative exposure to said individual patient exceeds a predetermined threshold stored in said database; and
presenting to a user on a display, prior to another imaging study on said individual patient, at least two of the following options: 1) specialized relatively low-dose protocols, 2) imaging examinations without ionizing radiation, or 3) analysis of future imaging examination requests, on condition that said processor determines that said cumulative exposure to said individual patient exceeds said stored predetermined threshold; and
a processor which executes the program.

30. A non-transitory computer-readable medium whose contents cause a computer system to execute instructions of a program, the program comprising the steps of:
retrieving quality assurance and exposure parameters from a database of a computer system;
receiving information on technical variables, including radiation exposure parameters, from imaging equipment in the performance of an imaging study on an individual patient, said information which is stored in said database;
determining, using a processor, whether a cumulative exposure to said individual patient exceeds a predetermined threshold stored in said database; and
presenting to a user on a display, prior to another imaging study on said individual patient, at least two of the following options: 1) specialized relatively low-dose protocols, 2) imaging examinations without ionizing radiation, or 3) analysis of future imaging examination requests, on condition that said processor determines that said cumulative exposure to said individual patient exceeds said stored predetermined threshold.

* * * * *